United States Patent
Chang

(10) Patent No.: US 11,752,151 B2
(45) Date of Patent: Sep. 12, 2023

(54) METHOD FOR ENHANCING HAIR GROWTH

(71) Applicant: BUDDHIST TZU CHI MEDICAL FOUNDATION, Hualien (TW)

(72) Inventor: Chung-Hsing Chang, Hualien (TW)

(73) Assignee: BUDDHIST TZU CHI MEDICAL FOUNDATION, Hualien (TW)

( * ) Notice: Subject to any disclaimer, the term of this patent is extended or adjusted under 35 U.S.C. 154(b) by 79 days.

(21) Appl. No.: 17/372,649

(22) Filed: Jul. 12, 2021

(65) Prior Publication Data
US 2023/0024910 A1    Jan. 26, 2023

(51) Int. Cl.
| | |
|---|---|
| *A61K 31/506* | (2006.01) |
| *A61P 17/14* | (2006.01) |
| *A61K 31/4439* | (2006.01) |
| *A61K 31/472* | (2006.01) |
| *A61K 9/00* | (2006.01) |
| *A61K 31/404* | (2006.01) |

(52) U.S. Cl.
CPC ........... *A61K 31/506* (2013.01); *A61K 9/0014* (2013.01); *A61K 31/404* (2013.01); *A61K 31/4439* (2013.01); *A61K 31/472* (2013.01); *A61P 17/14* (2018.01)

(58) Field of Classification Search
CPC .............................. A61K 31/506; A61P 17/14
See application file for complete search history.

(56) References Cited

U.S. PATENT DOCUMENTS 10,376,511 B2 *   8/2019   Ben Neriah ............ A61P 35/02

OTHER PUBLICATIONS

Yuan et al. Biochemical and Biophysical Research Communications, 2020, vol. 523, pp. 809-815 (Year: 2020).*

* cited by examiner

*Primary Examiner* — James D. Anderson
(74) *Attorney, Agent, or Firm* — Winston Hsu

(57) ABSTRACT

Provided is a method for enhancing hair growth through modulating a hair follicle cycle in a subject in need thereof. The method includes inhibition of casein kinase $1\alpha$ in an area of skin in the subject. Also provided is a method for increasing hair pigmentation in a subject in need thereof.

11 Claims, 31 Drawing Sheets
(24 of 31 Drawing Sheet(s) Filed in Color)

METHOD FOR ENHANCING HAIR GROWTH

BACKGROUND

1. Technical Field

The present disclosure relates to methods for enhancing hair growth by inhibiting casein kinase 1α (CK1α). Also provided herein are methods for modulating phases of a hair cycle and methods for increasing hair pigmentation by inhibiting casein kinase 1α.

2. Description of Related Art

Hair has important physiological functions. For example, hair coat keeps most mammals warm, dry and protected from harmful elements. Throughout the lifetime of an animal, hairs grow through a cyclic repetition of different phases of hair follicles, including telogen (a quiescence or resting phase), anagen (a regeneration or active hair growth phase) and catagen (a degeneration or transitional phase). At the end of telogen, the hair is shed, and a new hair replaces the original one, resulting in the start of the growing cycle again. Each follicle has its own life cycle that can be influenced by age, disease, and a wide variety of other factors.

However, hair loss or inadequate hair growth is a common problem experienced by many humans as well as many animals. The hair follicle cycle is regulated by both intrinsic and extrinsic signals which control quiescence and activation of hair follicle stem cells (HFSCs). Inadequate HFSC activation and proliferation underlie alopecia in numerous biological and pathological conditions, including aging. Molecules that can promote HFSC activation and anagen initiation have been intensely searched for, as they may both help reveal how hair regeneration is regulated and provide therapeutic and cosmetic interventions.

While there are approaches to this problem including such treatments as ultra-violet radiation, massage, psychiatric and exercise therapy, none of these, however, has been generally accepted as being effective. Even approaches such as revascularization surgery and acupuncture have shown little, if any, promise.

Recently, the most common approach for treating hair loss has been drug therapy. Many types of drugs ranging from vitamins to hormones have been tried, and only very few is recognized for successful therapeutic effects. For instance, it has been known that androgenic hormone involves in the development of male pattern baldness; therefore, either systemic or topical application of an antiandrogenic hormone would provide an inhibiting action to prevent or treat the baldness. Nevertheless, antiandrogenic hormone is not as effective as expected.

As such, there remains an unmet need for providing compositions and methods for enhancing hair growth in a subject in need thereof that are effective and easy for application.

SUMMARY

In the present disclosure, a method for enhancing or stimulating hair growth on an area of skin in a subject in need thereof is provided, the method comprising inhibiting casein kinase 1α in the area of skin. In at least one embodiment, the casein kinase 1α is inhibited during a telogen phase of a hair follicle cycle. In some embodiments, the casein kinase 1α is inhibited during an anagen phase of a hair follicle cycle. In at least one embodiment of the present disclosure, the subject suffers from hair loss. In some embodiments, the hair loss is a hair loss due to nutritional deficiency, a drug-induced hair loss, a radiation-induced hair loss, a stress-induced hair loss, a genetic hair loss, an aging hair loss or a disease-induced hair loss. In some embodiments, the drug-induced hair loss is induced by a chemotherapy drug, lithium, arsenic, bismuth, boric acid, thallium, colchicine, retinoid, heparin, warfarin, β-blocker, an angiotensin-converting enzyme (ACE) inhibitor, a hormone, valproic acid, carbamazepine, phenytoin, cimetidine, an antithyroid drug, a cholesterol-lowering drug, interferon, an anti-infective agent, amphetamine, an antidepressant, an anti-fungal agent, an anti-seizure agent, a birth control agent, a vitamin A-based medication, a medication for Parkinson's disease, a medication for stomach or a nonsteroidal anti-inflammatory drug. In some embodiments, the disease-induced hair loss is due to an autoimmune disease, a thyroid disorder, a metabolic syndrome, an infection or a cancer. In some embodiments, the autoimmune disease is alopecia areata, lupus erythematosus, Sicca syndrome, scleroderma, Crohn's disease, inflammatory bowel disease or psoriasis.

In some embodiments, the subject suffers from alopecia. In some embodiments, the alopecia is selected from the group consisting of androgenetic alopecia, alopecia areata, anagen effluvium, self-induced hair loss, telogen effluvium, and scarring alopecia.

In at least one embodiment of the present disclosure, inhibition of casein kinase 1α comprises inhibiting gene expression of casein kinase 1α in the area of skin. In some embodiments, the inhibition comprises topical application of a casein kinase 1α inhibitor to the area of skin. In some embodiments, the casein kinase 1α inhibitor is selected from the group consisting of D4476, IC261, CKI7 and a compound represented by formulas II to VII below:

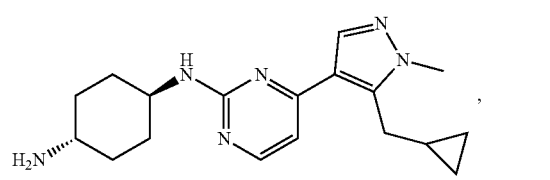

(II)

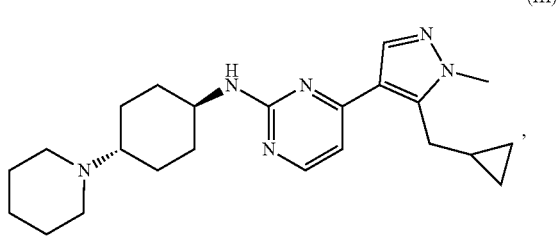

(III)

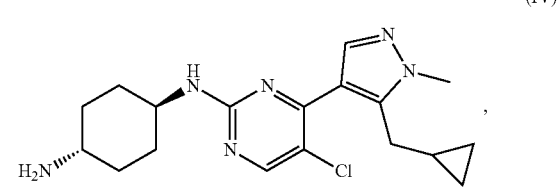

(IV)

-continued

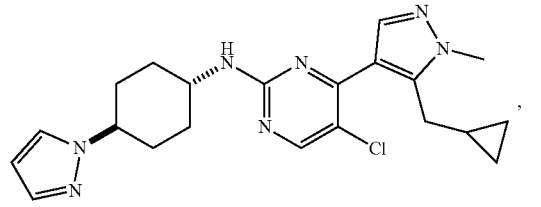
(V)

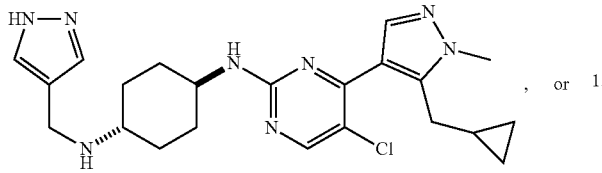
, or
(VI)

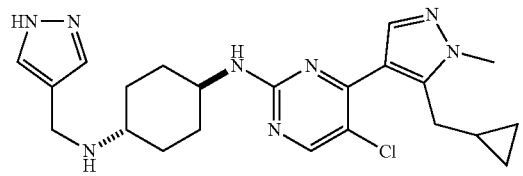
.
(VII)

In some embodiments, hair loss is resulted by delayed or slow growth of hair, or premature falling of hair. In at least one embodiment, the present disclosure provides a method to treat hair loss in different stages of a hair follicle cycle. In at least one embodiment of the present application, a method for modulating a hair follicle cycle in a skin area of a subject in need thereof is provided, comprising inhibiting casein kinase 1α in the skin area. In an embodiment, the modulation of the hair follicle cycle is inducing the hair follicle cycle into an anagen phase, wherein the hair follicles are in a telogen phase before inhibition of casein kinase 1α in the skin area. In some embodiments, the modulation of the hair follicle cycle is prolonging an anagen phase of the hair follicles, wherein the hair follicles are in an anagen phase before inhibition of casein kinase 1α in the skin area.

In at least one embodiment of the present disclosure, a method for increasing hair pigmentation in an area of skin in a subject in need thereof is provided, comprising inhibiting casein kinase 1α in the area of skin.

BRIEF DESCRIPTION OF THE DRAWINGS

This patent application/patent file contains at least one drawing executed in color. Copies of this patent or patent application publication with color drawing(s) will be provided by the Office upon request and payment of the necessary fee.

The present disclosure will become more readily appreciated by reference to the following descriptions in conjunction with the accompanying drawings.

FIG. 1A shows the experiment scheme. FIG. 1B shows the phenotypes of mice at week 7 (W7) before and after shaving, 8 (W8), 9 (W9), 10 (W10), 11 (W11) and 12 (W12). FIG. 1C shows the H&E staining, and FIG. 1D shows the β-catenin staining of the skin samples harvested at indicated weeks of age.

FIG. 2A shows experiment scheme. FIG. 2B shows the phenotypes of mice at week 9 (W9) before and after shaving, 10 (W10), 12 (W12), 13 (W13) and 16 (W16). FIG. 2C shows the H&E staining. FIG. 2D shows the β-catenin staining of the skin samples harvested. Arrows indicate the hair germs, where β-catenin was increased in the CK1αKO mice. FIG. 2E shows the BrdU staining.

FIG. 3A shows the experiment scheme, with 4-OH-TMX topically applied to mice on the back of mice after shaving at week 9. Phenotypes were recorded, and samples were obtained at week 9 (W9), 11 (W11) and 13 (W13). FIG. 3B shows the phenotypes of mice at week 9 (W9), 11 (W11) and 13 (W13). FIG. 3C shows the H&E staining, and FIG. 3D shows the β-catenin staining of the skin samples harvested at indicated timing; "D" indicates number of days after induction.

FIG. 4A shows the experiment scheme, wherein A51 was topically applied on back skin of the mice for 2 or 3 times during week 8 after the back hair of mice were shaved. Arrows indicating at weeks 9, 10 and 11 show the timing for sampling. FIG. 4B shows the phenotypes of mice in weeks 8 (W8), 9 (W9), 10 (W10) and 12 (W12). 0.1*2Q.O.D.: 0.1 mg each time every other day for a total of 0.2 mg; N indicates the number of mice in each group. FIG. 4C shows the H&E staining, and FIG. 4D shows the β-catenin staining of the skin samples harvested. FIGS. 4E and 4F show Fontana-Masson staining of hair follicle pigmentation at high magnification and low magnification, respectively.

FIG. 5A shows the experiment scheme, in which D4476 or IC261 was topically applied on back skin of the mice every other day at 0.04 mg each time with a total of 0.12 mg applied. Arrows indicating at weeks 9 and 10 show the timing for sampling. FIG. 5B shows the phenotypes of mice in weeks 8 (W8), 9 (W9) and 10 (W10). FIG. 5C shows the H&E staining, and FIG. 5D shows the β-catenin staining of the skin samples harvested. FIG. 5E shows Fontana-Masson staining of hair follicle pigmentation.

FIG. 6A shows the experiment scheme, with 4-OH-TMX topically applied to mice on the back of mice after shaving at week 4. FIG. 6B shows the phenotypes of mice in weeks 4 (W4), 6 (W6), 7 (W7) and 8 (W8), and FIG. 6C shows the result of H&E and β-catenin staining at week 8.

FIGS. 7A to 7H show that CK1α ablation in keratinocytes produces pigmented hair on MC1R mutated mice. FIG. 7A shows the scheme of crossing to obtain the MC1R mutated mice with CK1α ablation in keratinocytes. The MC1R mutated mouse with yellow coat color was crossed with K14-CreER;CK1α$^{f/f}$ mouse to generate K14-CreER;CK1α$^{f/f}$;MC1R$^{KI/KI}$ mouse. FIG. 7B shows the scheme of intraperitoneal injection of TMX to ablate CK1α in keratinocytes of the K14-CreER;CK1α$^{f/f}$;MC1R$^{KI/KI}$ mouse. FIG. 7C shows the phenotype of hair color on the back of MC1R mutated mice (Mc1r$^{em1}$) and MC1R mutated mice with CK1α ablation in keratinocytes (Mc1r$^{em1}$ X K14:: CK1αKO). FIG. 7D shows the hair shaft pigmentation under microscopy. FIGS. 7E and 7F show the hair follicle pigmentation with Fontana-Masson staining and the number of Fontana-Masson-stained cells, respectively. FIGS. 7G and 7H show the Western blotting analysis of expression levels of proteins in the KitL/c-Kit pathway in the back skin of mice and the quantitated expression levels in histograms, respectively.

DETAILED DESCRIPTIONS

Figure 1A:
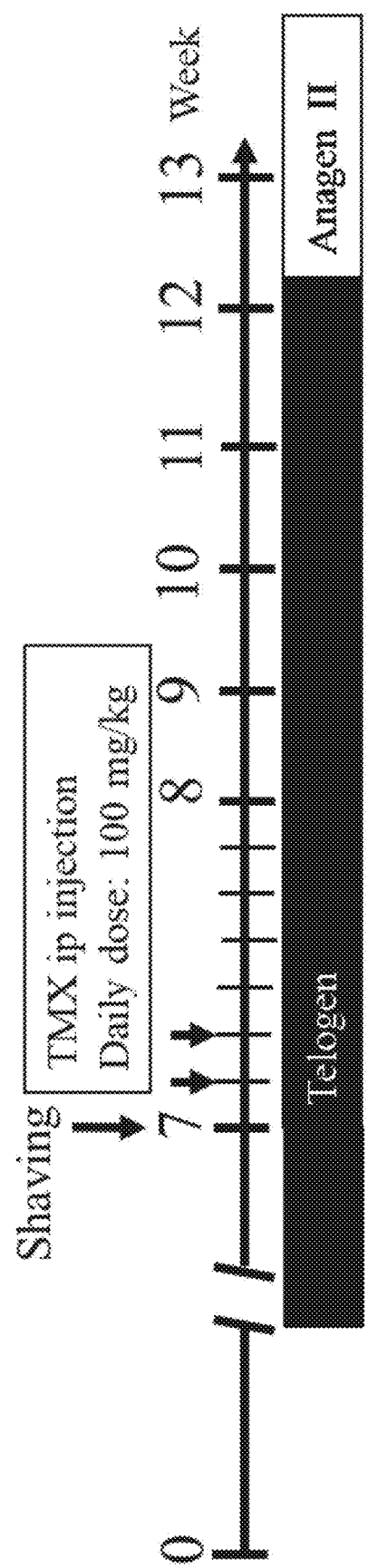
FIGS. 1A to 1D show results of intraperitoneal (i.p.) tamoxifen (TMX) induction of CK1α ablation in keratinocytes of K14-Cre-ERT2-CK1α$^{fl/fl}$ mice (CK1αKO) at 7 weeks old, the early phase of telogen.

The following examples are used for illustrating the present disclosure. A person skilled in the art can easily conceive the other advantages and effects of the present disclosure, based on the disclosure of the specification. The present disclosure can also be implemented or applied as described in different examples. It is possible to modify or alter the above examples for carrying out this disclosure without contravening its scope, for different aspects and applications.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs. However, the terms may have different meanings according to an intention of one of ordinary skill in the art, case precedents, or the appearance of new technologies. Also, some terms may be arbitrarily selected by the applicant, and in this case, the meaning of the selected terms will be described in detail in the descriptions of the present disclosure. Thus, the terms used herein have to be defined based on the meaning of the terms together with the descriptions throughout the specification.

It is further noted that, as used in this disclosure, the singular forms "a," "an," and "the" include plural referents unless expressly and unequivocally limited to one referent. The term "or" is used interchangeably with the term "and/or" unless the context clearly indicates otherwise.

Also, when a part "includes" or "comprises" a component or a step, unless there is a particular description contrary thereto, the part can further include other components or other steps, not excluding the others.

The terms "subject," "patient" and "individual" are used interchangeably herein and refer to a warm-blooded animal including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In some embodiments, the subject is a human.

The term "therapeutically effective amount" or "effective amount" is meant to include the amount of a compound that, when administered to a subject, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier" or "physiologically acceptable excipient" refers to a cosmetically or pharmaceutically acceptable material, composition, or vehicle, such as a liquid or solid filler, diluent, solvent, or encapsulating material. In some embodiments, each component is "pharmaceutically acceptable" in the sense of being compatible with the other ingredients of a cosmetic or pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, e.g., Remington: The Science and Practice of Pharmacy, 22nd ed.; Allen Ed.: Philadelphia, Pa., 2012; Handbook of Pharmaceutical Excipients, 7th ed.; Rowe et al., Eds.; The Pharmaceutical Press and the American Pharmaceutical Association: 2012; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, Fla., 2009.

The term "about" or "approximately" means an acceptable error for a given value as determined by one of ordinary skill in the art, which depends in part on how the value is measured or determined. In some embodiments, the term "about" or "approximately" means within 1, 2, 3, or 4 standard deviations. In some embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "drug," "cosmetic agent" and "therapeutic agent" refer to a compound or a cosmetical or pharmaceutical composition thereof, which is administered to a subject for preventing, ameliorating or treating one or more symptoms of a disorder, disease, or condition.

In some embodiments of the present disclosure, the methods provided herein comprise treating a subject regardless of patient's age, although some diseases or disorders are more common in certain age groups.

CK1 inhibitors (CKIs) of the present disclosure may have at least twice, at least 5 times, or at least 10 times the inhibitory activity towards CK1 as compared to other kinases such as cyclin-dependent kinases (CDKs) regulating the cell cycle, (e.g., Cdk2, Cdk4, and Cdk6). In addition, CK1 inhibitors have at least twice, at least 5 times, or at least 10 times the inhibitory activity towards CK1 as compared to protein kinase C (PKC), protein kinase A (PKA), epidermal growth factor receptor 2 (HER2), rapidly accelerated fibrosarcoma 1 (RAF-1), mitogen-activated protein kinase 1 (MEK1), mitogen-activated protein kinase (MAP kinase), epidermal growth factor receptor (EGF receptor), platelet-derived growth factor receptor (PDGF receptor), insulin-like growth factor receptor (IGF receptor), phosphoinositide 3 kinase (PI3 kinase), Wee1 kinase, Src, and/or Abl.

CKI are selective towards CK1-α (CSNK1A; at the genomic, mRNA or protein level, GenBank Accession Nos. NP_001020276, NM_001025105 and NM_001020276). Thus, for example, such CK1 inhibitors have at least twice, at least 5 times, or at least 10 times the inhibitory activity towards CK1-α as compared to CK1-δ and CK1-ε.

In at least one embodiment of the present disclosure, a casein kinase 1 inhibitor is represented by the following general formula I, including any stereoisomer or salt thereof:

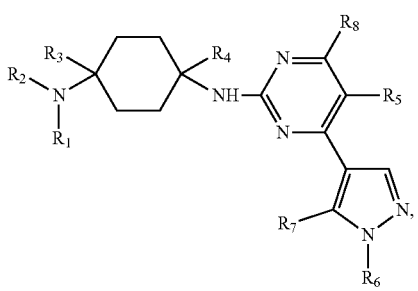

(I)

wherein:
- $R_1$ and $R_2$ are each independently selected from the group consisting of H, straight or branched C1-C8 alkyl, straight or branched C1-C5 alkoxy, straight or branched C1-C5 acyl, C5-C15 aryl, and C3-C7 heteroaryl each optionally substituted by at least one of halide, hydroxyl, ester, ether, C5-C15 aryl, C3-C7 heteroaryl, and amide; or $R_1$ and $R_2$ together with the nitrogen atom they are connected to form a 4 to 7 membered saturated, unsaturated or aromatic ring that may optionally include at least one of N, O, NH, C=N, C=O and $SO_2$ and can optionally be substituted with at least one of straight or branched C1-C5 alkyl, C5-C15 aryl, C3-C7 heteroaryl, hydroxyl, halide and cyano;
- $R_3$ and $R_4$ are each independently selected from the group consisting of H, straight or branched C1-C8 alkyl optionally substituted by at least one of halide, hydroxyl, alkoxy, C5-C15 aryl, C3-C7 heteroaryl, ester and amide; or
- $R_1$ or $R_2$ together with $R_3$ and the carbon and nitrogen atom they are each connected to form a 4 to 7 membered saturated, unsaturated or aromatic ring that may optionally include at least one of N, NH, O, C=N, C=O, and $SO_2$, and can optionally be substituted with at least one of straight or branched C1-C5 alkyl, C5-C15 aryl, C3-C7 heteroaryl, hydroxyl, carbonyl, and halide;
- $R_5$ and $R_8$ are each independently selected from the group consisting of H, halide, straight or branched C1-C8 alkyl, straight or branched C2-C8 alkenyl, and straight or branched C2-C8 alkynyl optionally substituted by at least one halide;
- $R_6$ is selected from straight or branched C1-C8 alkyl, straight or branched C2-C8 alkenyl, straight or branched C2-C8 alkynyl, C5-C10 cycloalkyl, and saturated or unsaturated 4 to 6 membered heterocycle optionally substituted by at least one of straight or branched C1-C8 alkyl, C3-C7 cycloalkyl, 4 to 6 membered heterocycle, C5-C15 aryl, C3-C7 heteroaryl, halide, hydroxyl, and C1-C5 alkyl halide;
- $R_7$ is selected from the group consisting of straight or branched C1-C8 alkyl, straight or branched C2-C8 alkenyl, and straight or branched C2-C8 alkynyl optionally substituted by at least one of C3-C7 cycloalkyl, 4 to 6 membered heterocycle, C5-C15 aryl, C3-C7 heteroaryl, halide, hydroxyl, and C1-C5 alkyl halide.

Additional casein kinase I inhibitors include those described in International Publication No. WO 2017/021969; the disclosure of which is incorporated herein by reference in its entirety.

The cosmetical or pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the cosmetical or pharmaceutical compositions provided herein can also comprise liposomes, micelles, microspheres, nanosystems, and any mixtures thereof.

Cosmetically or pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The cosmetical or pharmaceutical compositions can also be administered topically by electroporation, iontophoresis, phonophoresis, sonophoresis, microneedle or needle-free injection, such as PowderTect (Chiron Corp., Emeryville, Calif.) and Bioject (Bioject Medical Technologies Inc., Tualatin, Oreg.).

The cosmetical or pharmaceutical compositions provided herein can be provided in the forms of ointments, creams, and gels. Suitable ointment vehicles include oleaginous or hydrocarbon vehicles, including lard, benzoinated lard, white petrolatum, olive oil, cottonseed oil, and other oils; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, e.g., Remington: The Science and Practice of Pharmacy). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Suitable gels may be semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and Carbopol; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gums; sodium alginate; and gelatin. In order to prepare a uniform gel, dispersing agents such as alcohol or glycerin can be added, or the gelling agent can be dispersed by trituration, mechanical mixing, and/or stirring.

EXAMPLES

Exemplary embodiments of the present disclosure are further described in the following examples, which should not be construed to limit the scope of the present disclosure.

Generally, the nomenclature used herein and the laboratory procedures utilized in the present disclosure include molecular, biochemical and recombinant DNA techniques. Such techniques are thoroughly explained in the literature. See, for example, "Molecular Cloning: A Laboratory Manual," Sambrook et al., (1989); "Current Protocols in Molecular Biology," Volumes I-III Ausubel, R. M., ed. (1994); "A Practical Guide to Molecular Cloning," John Wiley & Sons, New York (1988); Watson et al., "Recombinant DNA," Scientific American Books, New York; Birren et al. (eds) "Cell Biology: A Laboratory Handbook," Volumes I-III Cellis, J. E., ed. (1994); "Culture of Animal Cells—A Manual of Basic Technique," Freshney, Wiley-Liss, N.Y. (1994), Third Ed.; "Transcription and Translation," Hames, B. D., and Higgins S. J., eds. (1984); "Animal Cell Culture," Freshney, R. I., ed. (1986); "Immobilized Cells and Enzymes," IRL Press, (1986); "A Practical Guide to Molecular Cloning," Perbal, B., (1984) and "Methods in Enzymology," Vol. 1-317, Academic Press; "PCR Protocols: A Guide to Methods and Applications," Academic Press, San Diego, Calif. (1990); Marshak et al., "Strategies for Protein Purification and Characterization—A Laboratory Course Manual," CSHL Press (1996); all of which are incorporated by reference as if fully set forth herein. Other general references are provided throughout this disclosure. The procedures therein are believed to be well known in the art and are provided for the convenience of the reader. All the information contained therein is incorporated herein by reference.

Materials and Methods

Mice

K14-Cr-ERT2-CK1$\alpha^{fl/fl}$ mice, MC1R mutated mice (Mc1r$^{em1}$) and MC1R mutated mice with CK1$\alpha$ ablation in keratinocytes (Mc1r$^{em1}$ X K14::CK1$\alpha$KO) were collaboratively generated in National Laboratory Animal Center (NLAC) in Tainan, Taiwan, and wild type C57BL/6J mice were also purchased from NLAC. Experiments and animal caring were performed in the Laboratory Animal Center, Tzu Chi University, Hualien, Taiwan, with the approval of Animal Care Committee in accordance with legal and ethical standards. Both male and female mice were used. The hair cycle in wild C57BL/6J mice is related to the age; weeks 4 to 6 are an anagen phase, weeks 6 to 7 are a catagen phase, and weeks 7 to 12 are a telogen phase.

Targeting Gene Activation (Induction of CK1$\alpha$ Ablation)

For deletion of CK1$\alpha$ expression in keratinocytes, K14-Cre-ERT2-CK1$\alpha^{fl/fl}$ mice were treated with 100 mg/kg tamoxifen (TMX) dissolved in corn oil (C8267; Sigma) two times by intraperitoneal injection, or topically treated with 4-hydroxyl-tamoxifen (4-OH-TMX) (H6278; Sigma), which was dissolved in 99.9% alcohol (32205; Sigma). 200 µL with the concentration of 3 mg/mL was administered to the back skin after shaving for 5 times/week.

Preparation of CK1$\alpha$ Inhibitors (CKI)

A51 is a gift from Dr. Yinon Ben-Nerian's lab (which was published in Cell, Volume 175, Issue 1, 20 Sep. 2018, pages 171-185). For topical application onto mouse skin, 1 mg of CKI was dissolved in 6 µL dimethyl sulfoxide (DMSO) and mixed with 54 µL of vehicle which contained 60% of white wax and 40% of paraffin oil. The final working concentration is 0.1 mg/cm$^2$.

D4476 was purchased from Sigma Aldrich (#D1944). For topical application onto mouse skin, 4 mg of CKI was dissolved in 1 mL DMSO as the stock. 10 µL stock was mixed with 40 µL of vehicle which contained 60% of white wax and 40% of paraffin oil. The final working concentration is 0.04 mg/cm$^2$.

IC261 was purchased from Sigma Aldrich (#40090). For topical application onto mouse skin, 4 mg of CKI was dissolved in 1 mL DMSO as the stock. 10 µL stock was mixed with 40 µL of vehicle which contained 60% of white wax and 40% of paraffin oil. The final working concentration is 0.04 mg/cm$^2$.

Topical Drug Treatment

Mice at 8 weeks old were shaved to remove hair on back skin and cleaned with 75% ethanol. Topical CKIs were applied on the back skin 3 times in one week, and the tissue was harvested on day 7, day 14 and some on day 28 after application of CKIs. The tissue was analyzed by the methods described below.

Histopathology, Immunohistochemical Staining, and Fontana-Masson Staining

Skin samples were harvested at indicated timings for tissue analysis. Paraffin-embedded specimens were cut into 5-µm sections. After deparaffinization (with tissue slides being soaked in xylene three times, each time for 5 min) and rehydration (with slides being incubated in the following graded series of ethanol: 100%, 100%, 95%, 90% and 70%, 5 min each), the slides were rinsed with distilled water for 5 min.

Hematoxylin & Eosin (H&E) Staining and Fontana-Masson Staining

Fontana-Masson staining and H&E staining were performed by using the kit from ScyTek Laboratories, Inc. according to the manufacturer's instructions.

Briefly, for Fontana-Masson staining, a freshly mixed ammoniacal silver solution was placed in a 58° C. to 60° C. water bath and allowed to equilibrate. The slides were incubated in a warmed ammoniacal silver solution for 30 to 60 min or until the tissue sections became yellow/brown in color, and were then rinsed with distilled water for 3 to 5 seconds (s). The slides were incubated in a gold chloride solution (0.2%) for 30 s and were then rinsed with distilled water for 3 to 5 s. The slides were incubated in a sodium thiosulfate solution (5%) for 1 min and were then rinsed with distilled water for 3 to 5 s. The slides were incubated in a nuclear fast red solution for 5 min, rinsed for 1 min in running tap water, dehydrated in four changes of fresh absolute alcohol (95%, 95%, 100% and 100%) and xylene, and mounted with Histokitt (Assistent).

For histopathology by H&E staining, skin tissues were fixed overnight in 10% neutral buffered formalin at 4° C. and then transferred to 70% ethanol before being processed and embedded in paraffin. Paraffin sections were then stained with H&E.

Immunohistochemical Staining

Paraffin sections were incubated in a humidity chamber for 15 min at 60° C. Sections were deparaffinized in two changes of xylene for 5 min each and hydrated in two changes of 100% ethanol for 5 min each, then in 95% and 80% ethanol for 5 min each, and finally rinsed in distilled water. Antigen retrieval was enhanced by microwaving the slides in a citrate buffer (DAKO; pH 6.0) for 20 min. Endogenous peroxidase activity was quenched with 3% hydrogen peroxide in methanol. After blocking, sections were incubated overnight at 4° C. with β-catenin antibody (1/100; BD Bioscience). Secondary antibodies used were horseradish peroxidase (HRP)-polymer anti-mouse antibodies (Nichirei). 3-Amino-9-ethylcarbazole (AEC) chromogen (ScyTek) was used for detection, and hematoxylin was used as a counterstain.

5-bromo-2'-deoxyuridine (BrdU) Staining

For labelling of proliferating cells in a mouse, intraperitoneal injection of 200 μL BrdU (Amersham; cell proliferation labelling reagent, RPN201, GE Healthcare) was performed. Six hours later, skin samples were harvested for paraffin embedding. 4 μm paraffin embedded sections were prepared as above, and then incubated with Target Retrieval Solution (pH 6.0) (DAKO, S1699) in a water bath for 20 min at 95° C. to 120° C. The staining dish was moved to room temperature, allowing the slides to cool to 30° C., followed by rinsing with PBS once. Then, the slides were incubated with primary antibody BrdU (Thermo Fisher Scientific, B23151, 1:100) at 4° C. overnight. The slides were rinsed with PBS for 3 times, 5 min each time. The slides were incubated with EnVision/HRP, Rabbit/Mouse (ENV) (DAKO, k5007) for 30 min, and rinsed with PBS for 3 times, 5 min each time. Then, the slides were incubated with AEC+ High Sensitivity Substrate Chromogen Ready-to-Use (DAKO, K3461) for 5 min, and washed with running water for 5 min. Then, the slides were counterstained with hematoxylin for 30 s to 1 min, and washed with running water for 10 min. The slides were mounted with Aqueous-Mount (ScyTek, 51934).

Example 1: Inhibition of CK1α Induces an Anagen Phase in a Hair Cycle

CK1α inhibitions in mice keratinocytes were carried out by various means, and all shown to induce anagen in a hair cycle from a telogen phase, early telogen (7 weeks) and middle telogen (9 weeks).

Figure 1B:
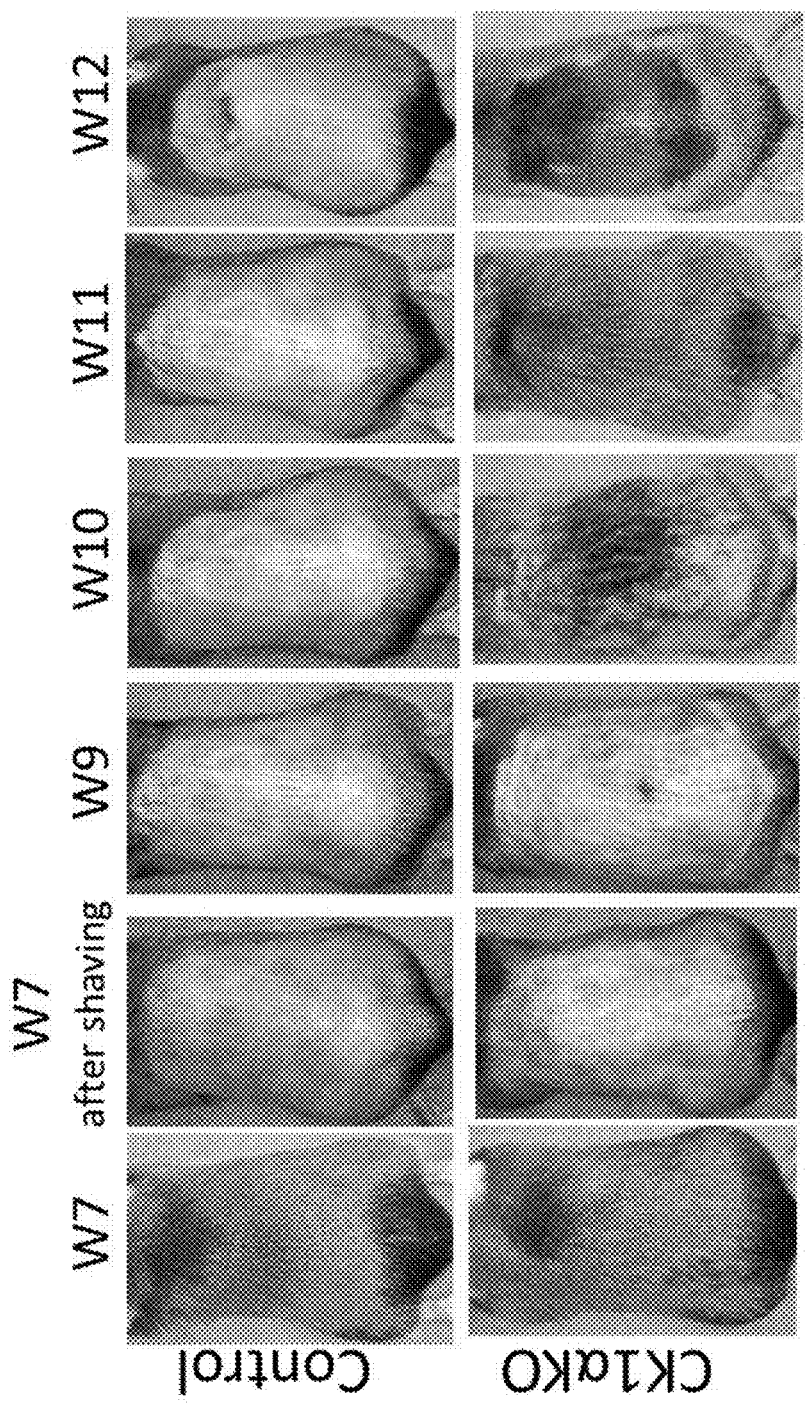
Figure 1C:
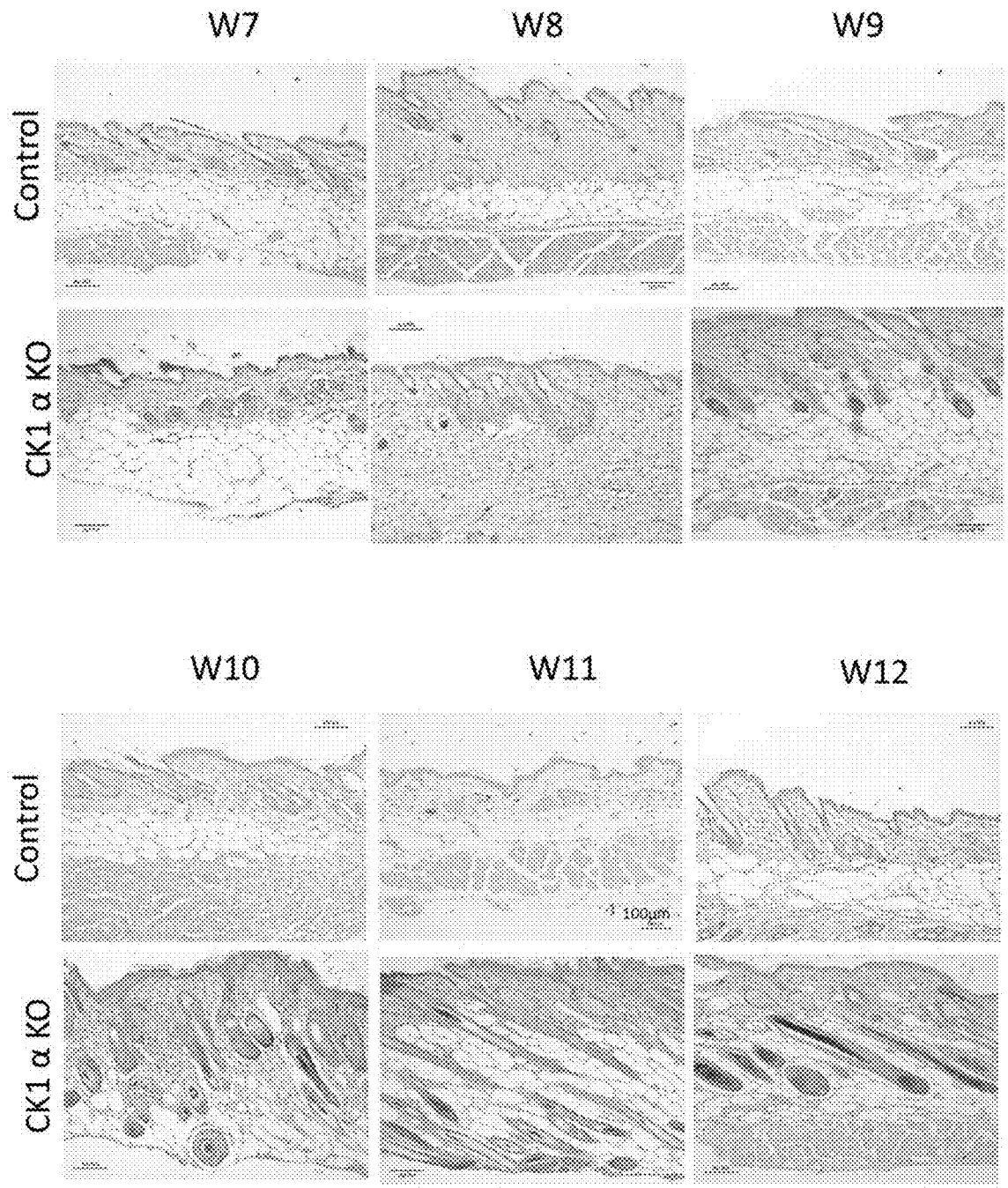
Figure 1D:
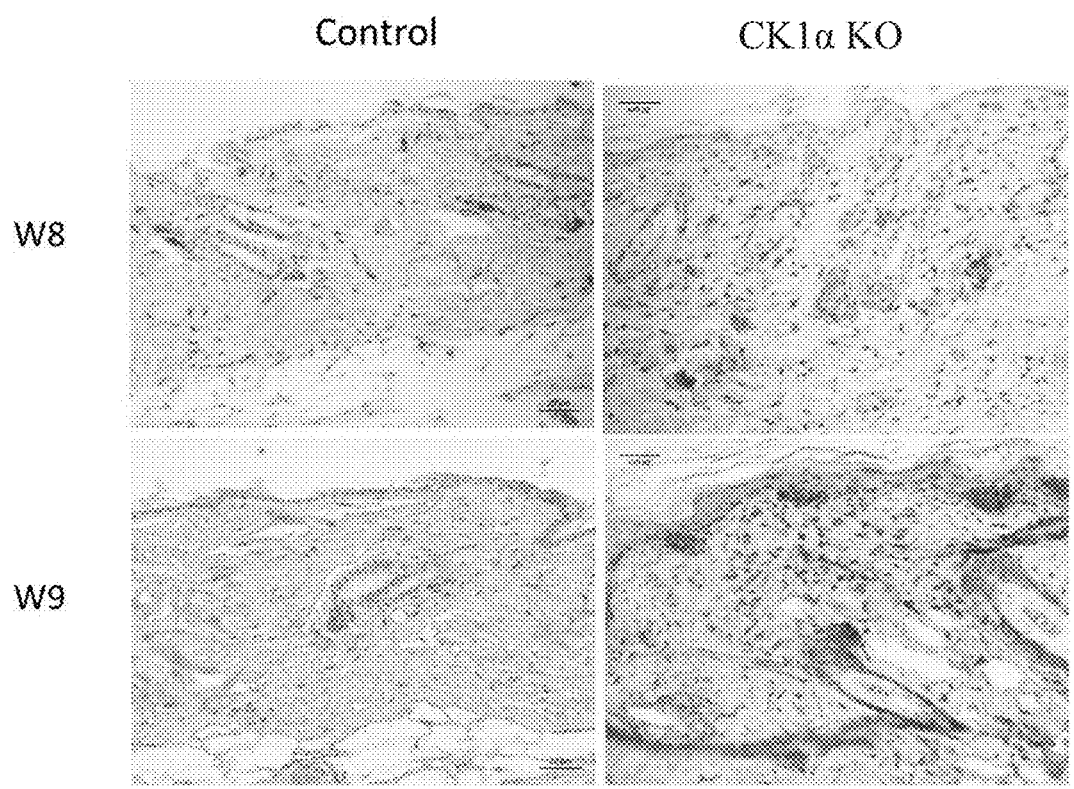

In the first study, K14-Cre-ERT2-CK1α$^{fl/fl}$ adult mice at 7 weeks old were used for intraperitoneal (i.p.) tamoxifen (TMX) induction to ablate CK1α expression in keratinocytes. FIG. 1A shows the study design, with the back hair of mice shaved at week 7 and TMX i.p. injection at a daily dose of 100 mg/kg on day 1 and day 2 after shaving. The phenotype and histology of mice skin sections were recorded every week from week 7 to week 12, as shown in FIGS. 1B and 1C, respectively. It was shown that in control mice (N=6), hair follicles of the mice back skin maintained in a telogen phase from week 7 to week 12. However, in CK1α-ablated mice (CK1αKO, N=6), an early anagen phase of hair follicles appeared as early as in week 8 or 9 and continuously developed into full anagen during week 10 to week 12. Wnt/β-catenin pathway operates on hair follicle precursor cells and serves as a proximal signal for the telogen-anagen transition. As shown in FIG. 1D, increased β-catenin staining was demonstrated in CK1α-ablated mice skins in week 8 and week 9, compared to that in control mice.

Figure 2A:
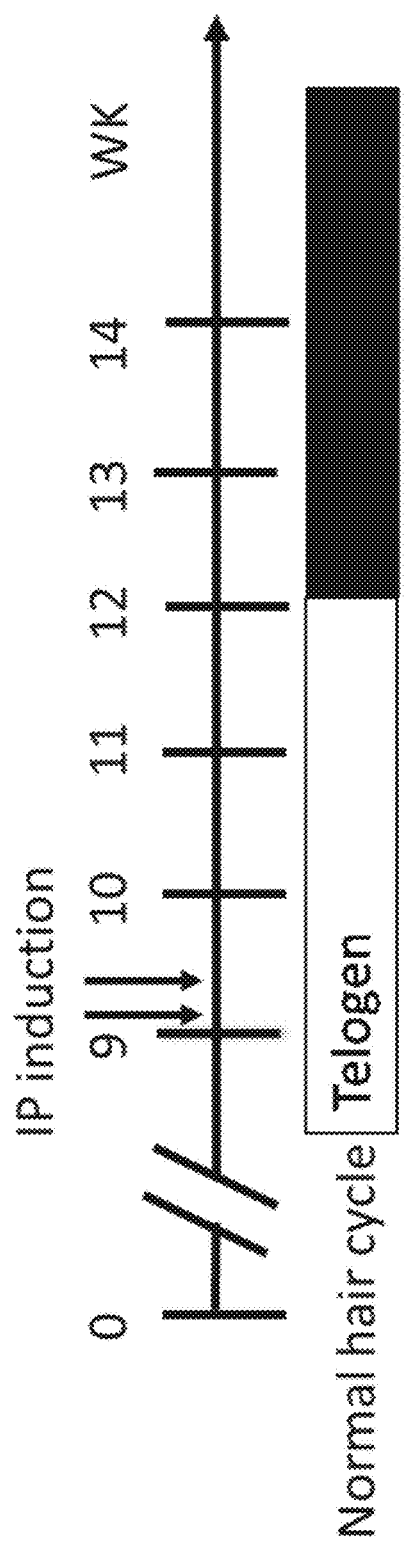
FIGS. 2A to 2E show results of intraperitoneal (i.p.) tamoxifen (TMX) induction of CK1α ablation in keratinocytes of K14-Cre-ERT2-CK1α$^{fl/fl}$ mice (CK1αKO) at 9 weeks old, the middle phase of telogen.
Figure 2B:
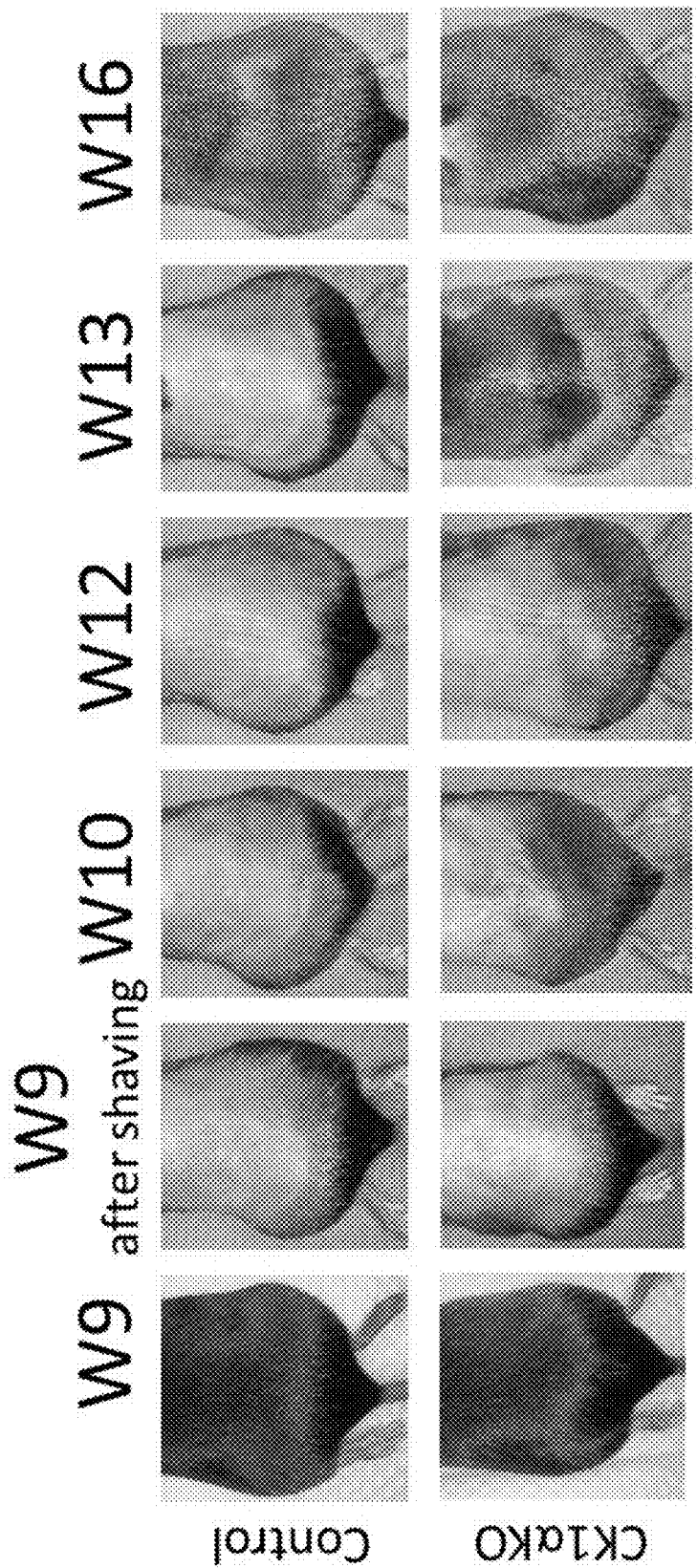
Figure 2C:
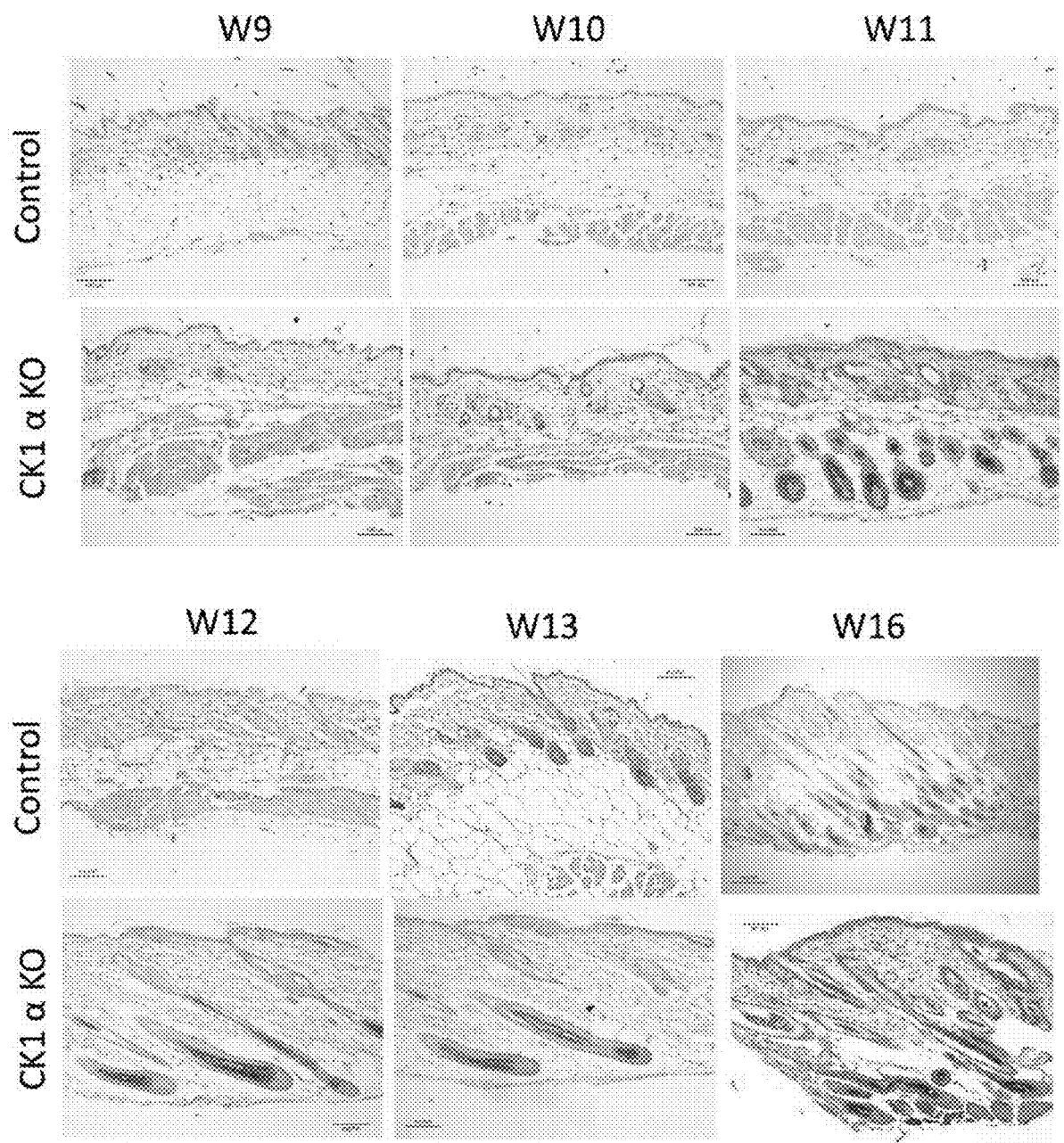
Figure 2D:
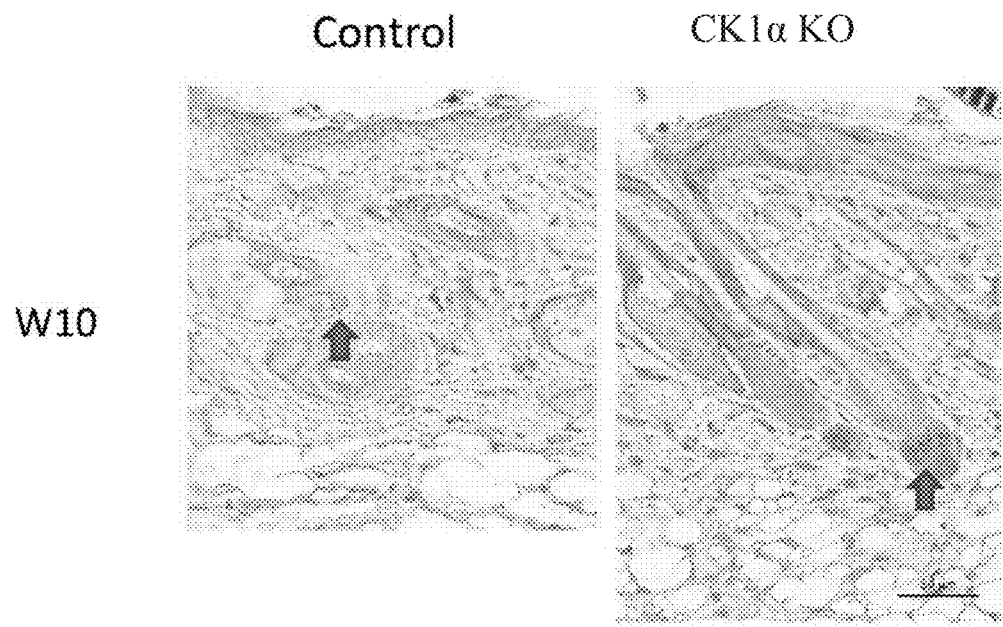
Figure 2E:
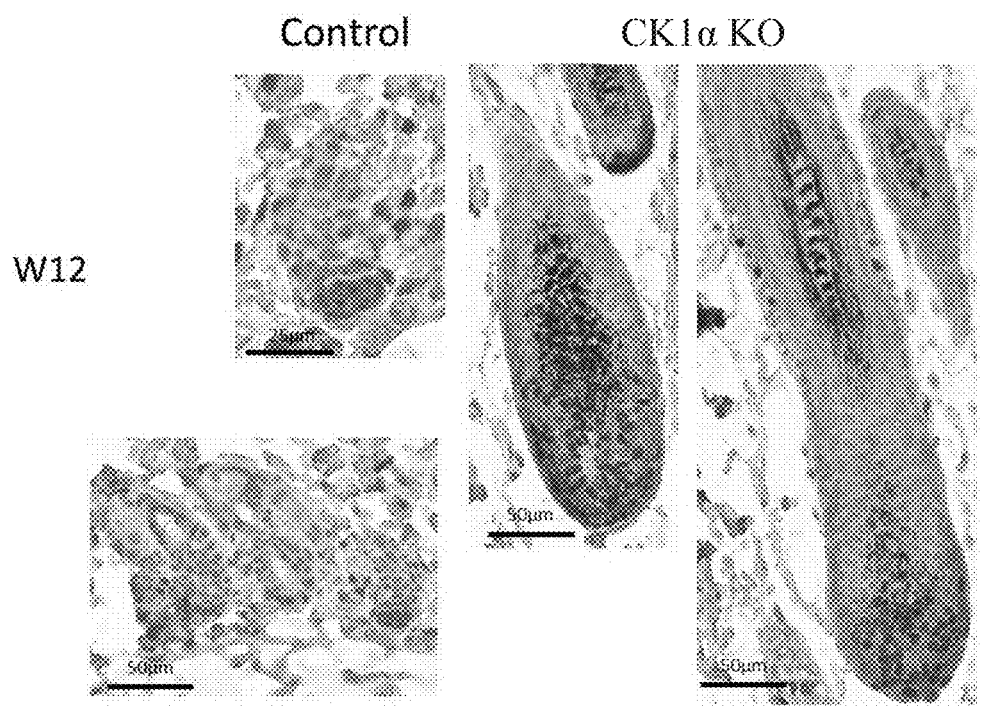

In the second study, K14-Cre-ERT2-CK1α$^{fl/fl}$ adult mice at 9 weeks old were used for intraperitoneal (i.p.) tamoxifen (TMX) induction to ablate CK1α expression in keratinocytes. FIG. 2A shows the study design, with the back hair of mice shaved at week 9 and TMX i.p. injection at a daily dose of 100 mg/kg on day 1 and day 2 after shaving. The phenotypes of the mice were recorded from week 9 to week 16, as shown in FIG. 2B, respectively. It was shown that in control mice (N=3), hair follicles of the mice back skin maintained in a telogen phase from week 9 to week 12, with an anagen phase starting in week 13. In week 16, visible hair was observed on the back of the control mice. By contrast, in CK1α-ablated mice (CK1αKO, N=3), an early anagen phase of hair follicles appeared between week 10 and week 11, with visible hairs grown starting in week 13. In week 16, the CK1α-ablated mice backs were fully covered with hair. FIG. 2C shows the histology of mice skin sections with H&E staining. It was shown that before i.p. TMX induction in week 9, both the normal mice and CK1αKO mice showed the hair follicles in a telogen phase. Then, a telogen phase continued from week 9 to week 11 or 12 in control mice with the anagen phase began at week 13 and fully developed at week 16. On the other hand, in CK1αKO mice, an anagen phase began at week 10 with continuously growing of hairs during week 11 to week 16. That is, CK1α inhibition during a telogen phase in keratinocytes induces and initiates an anagen phase of a hair cycle to start early. FIG. 2D shows the result of immunohistochemistry staining of β-catenin. Similar to the first study, increased β-catenin staining was demonstrated in CK1α-ablated mice skins in week 10, compared to that in control mice. FIG. 2E shows the result of immunohistochemical staining of 5-bromo-2'-deoxyuridine (BrdU), which labels the proliferative cells, where increased staining in the matrix of hair follicles was shown in CK1αKO mice compared to control mice.

Figure 3A:
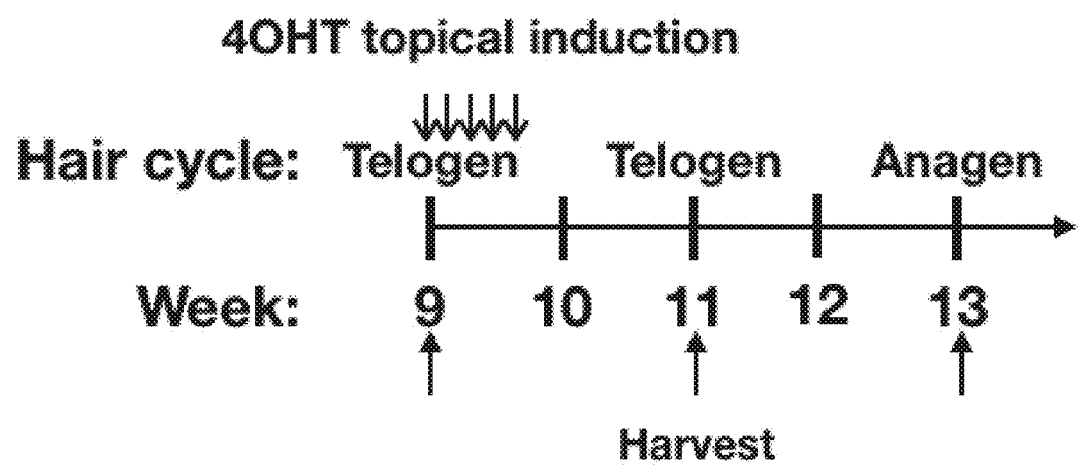
FIGS. 3A to 3D show results of topical induction of CK1α ablation in keratinocytes of K14-Cre-ERT2-CK1α$^{fl/fl}$ mice with 4-OH-TMX (CK1αKO).
Figure 3B:
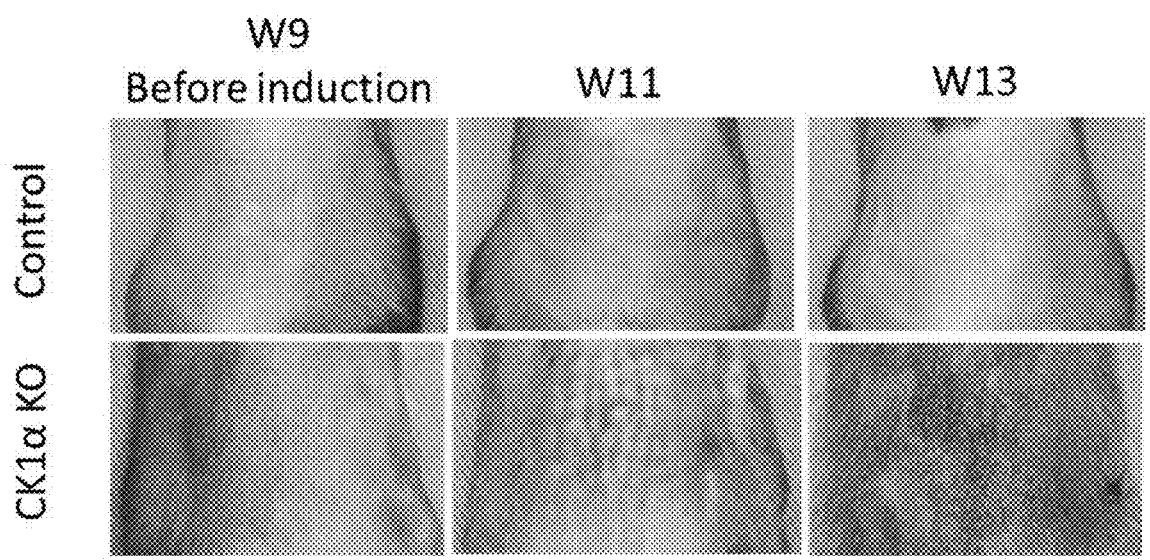
Figure 3C:
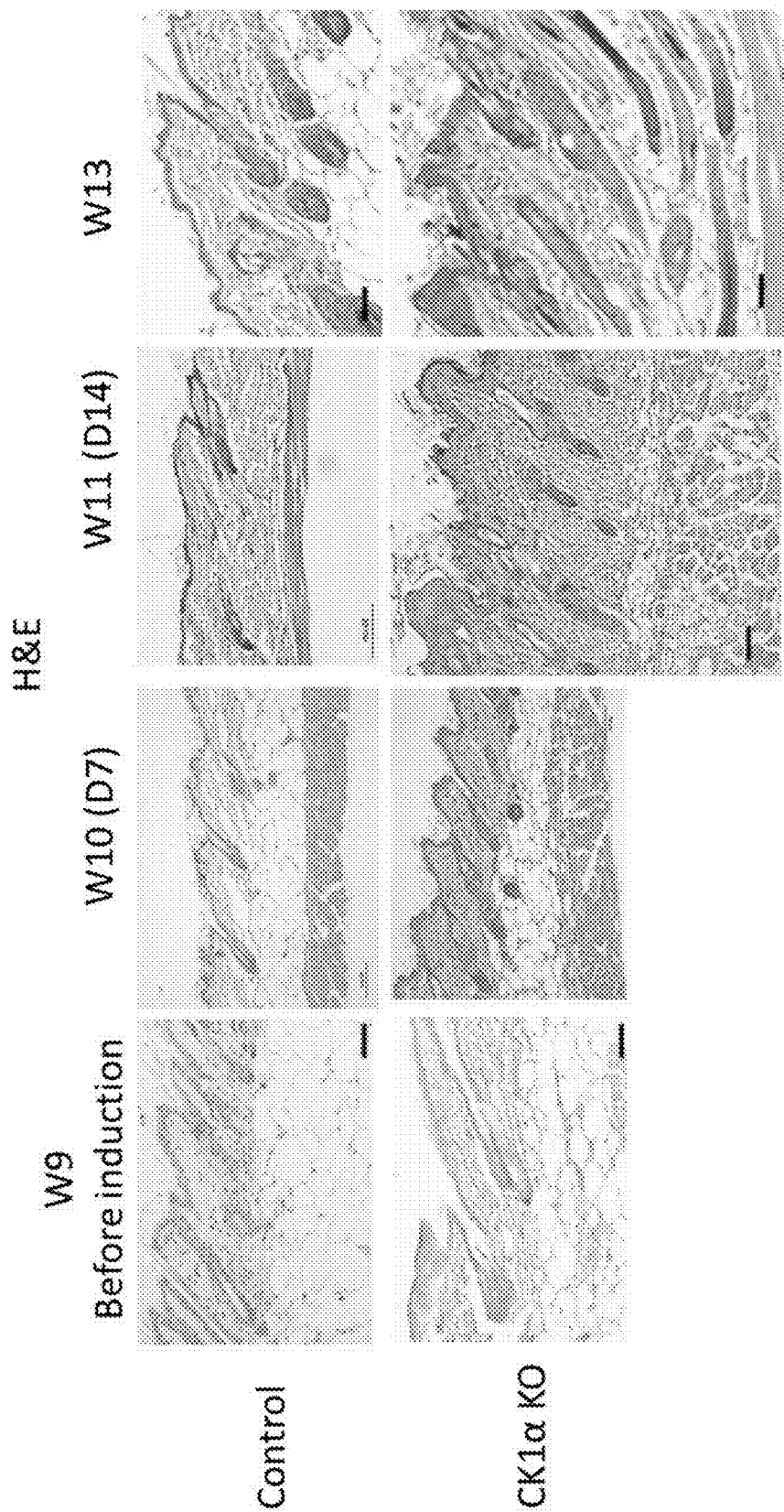
Figure 3D:
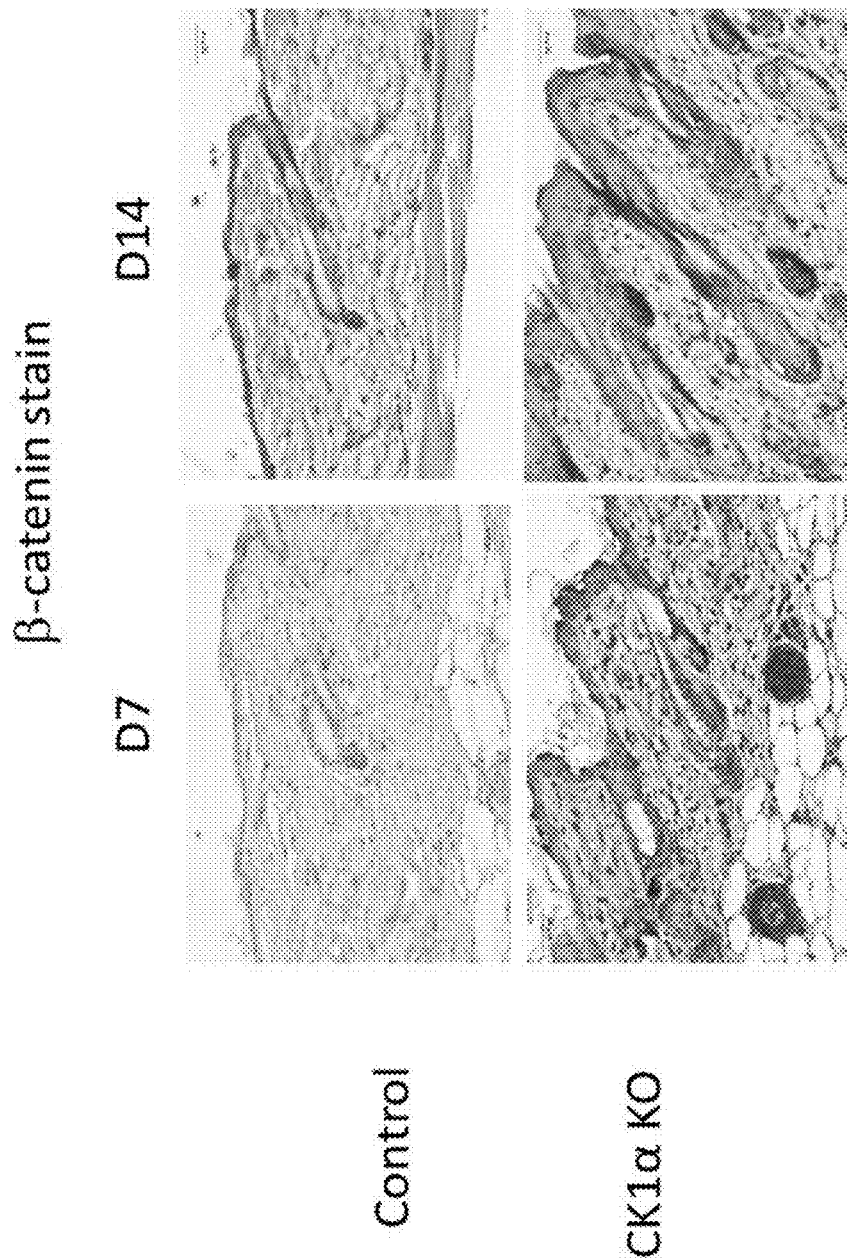

Next, 4-OH-TMX was used for topical induction of CK1α ablation in keratinocytes of the back skin of K14-Cre-ERT2-CK1α$^{fl/fl}$ mice. As shown in FIG. 3A, mice at 9 weeks old were used with their back hair shaved at week 9, followed by 4-OH-TMX topical induction on the shaved back skin. FIGS. 3B and 3C show the phenotypes and histology recorded from week 9 to week 13. In normal mice (N=5), a telogen phase was observed from week 9 to week 11, and anagen was noted to start in week 13. In CK1α-ablated mice (N=11), an anagen phase with elevated papules on skin surface in histology was noted on week 11, and visible hairs with fully developed anagen were noted in week 13. FIG. 3D shows the result of immunohistochemical staining of β-catenin. β-catenin expression in the hair germ at week 10 (W10) and week 11 (W11), which were day 7 (D7) and day 14 (D14) after induction of CK1αablation, was shown to increase in CK1αKO mice compared to control mice. β-catenin nuclear staining was shown on the basal layer of epidermis, secondary hair germ and matrix, indicating activation of Wnt/β-catenin signal during the telogen-anagen transition.

Figure 4A:
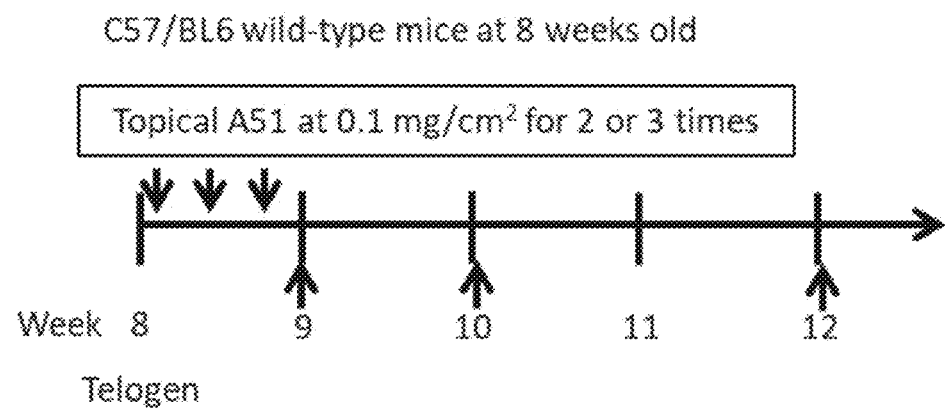
FIGS. 4A to 4F show an exemplary CK1α inhibitor, A51, in inducing hair growth and pigmentation in C57/BL6 wild-type mice at 8 weeks old.
Figure 4B:
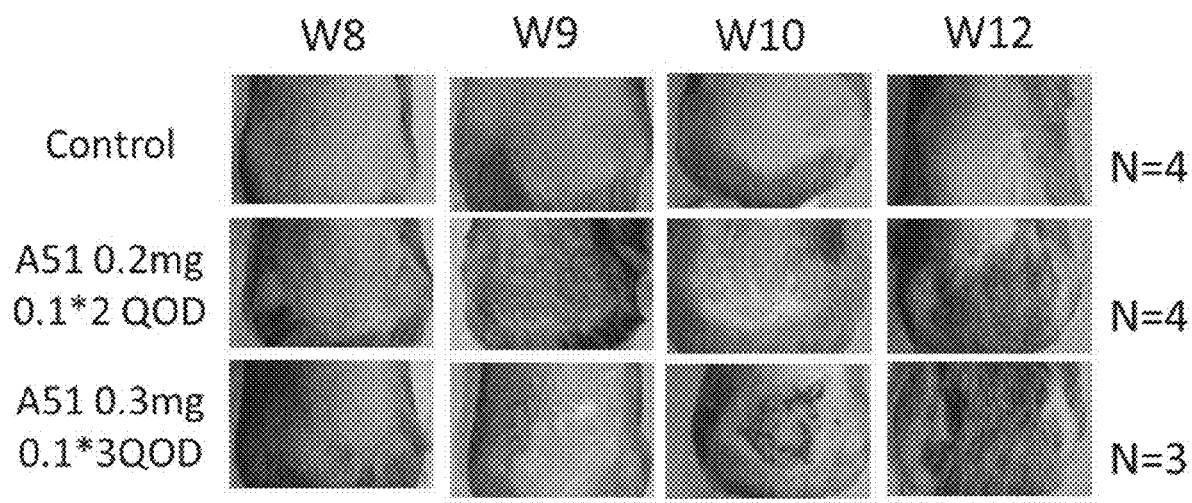
Figure 4C:
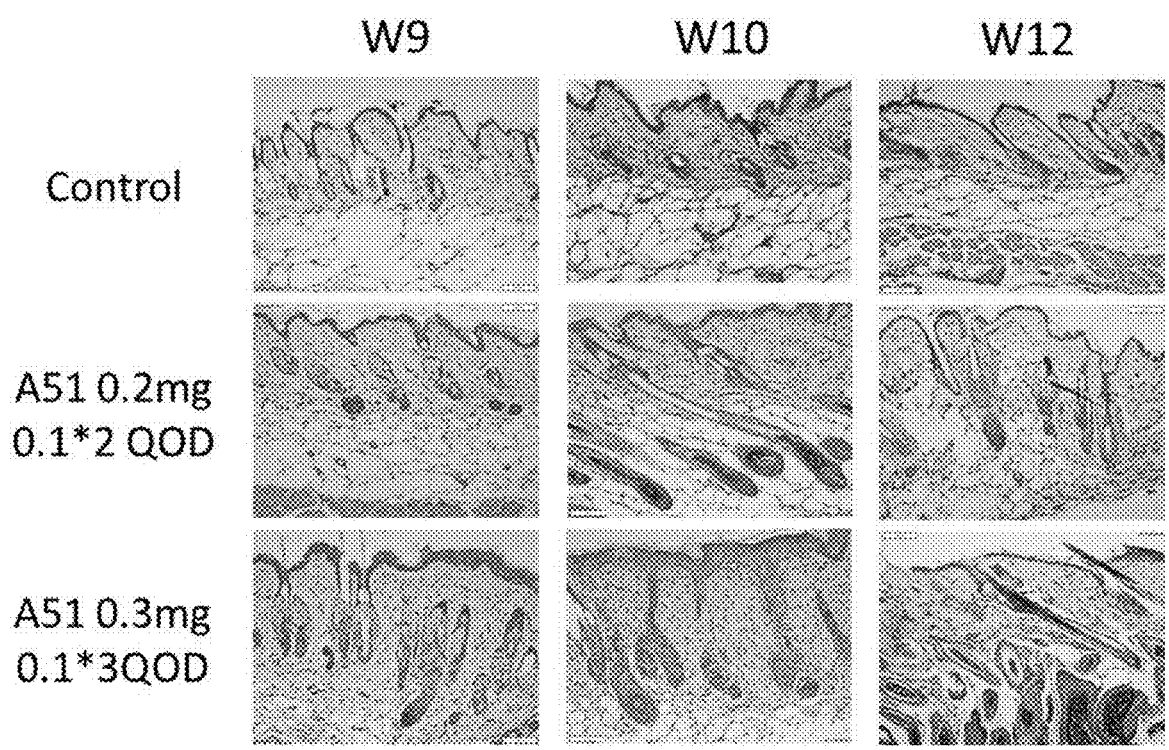
Figure 4D:
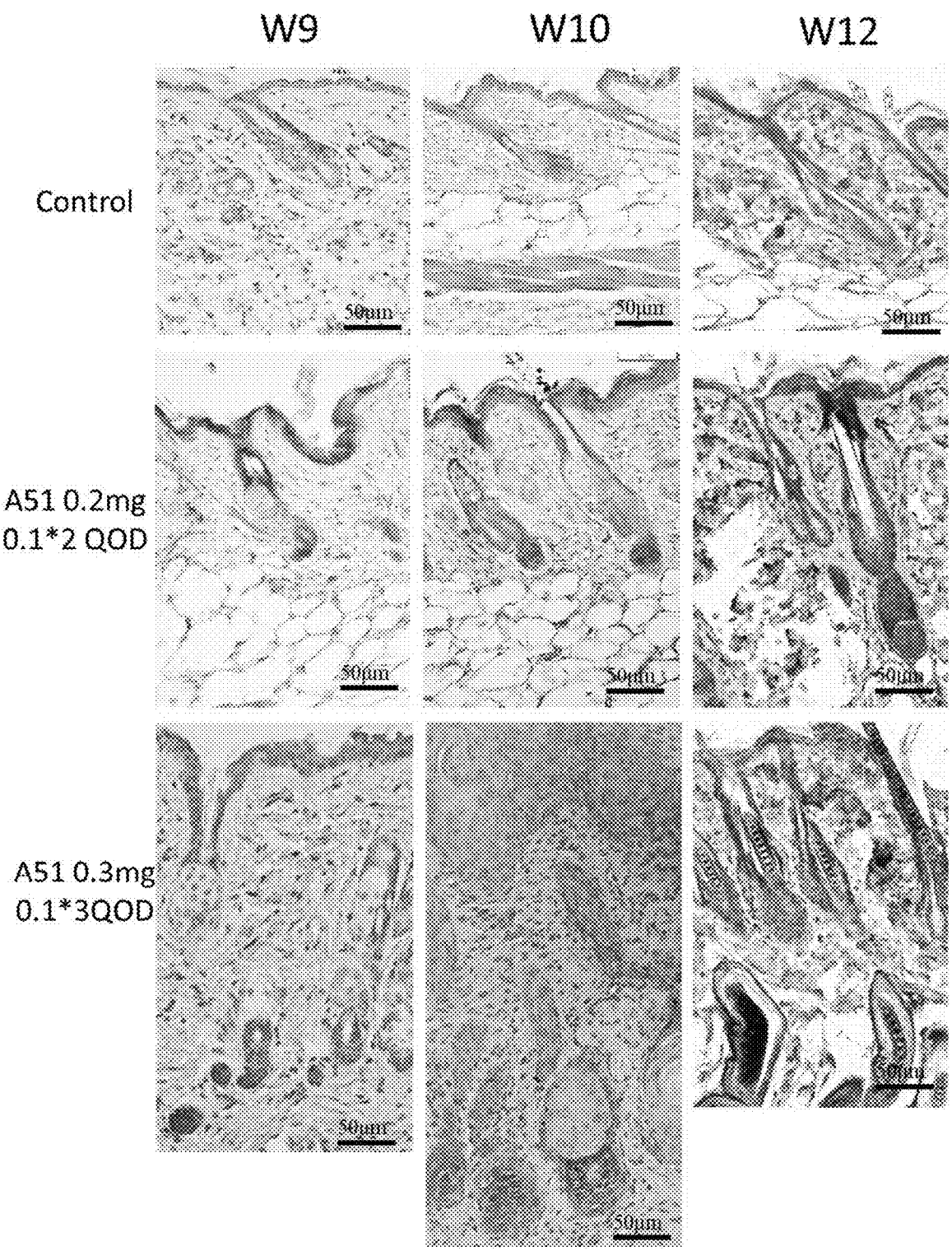
Figure 4E:
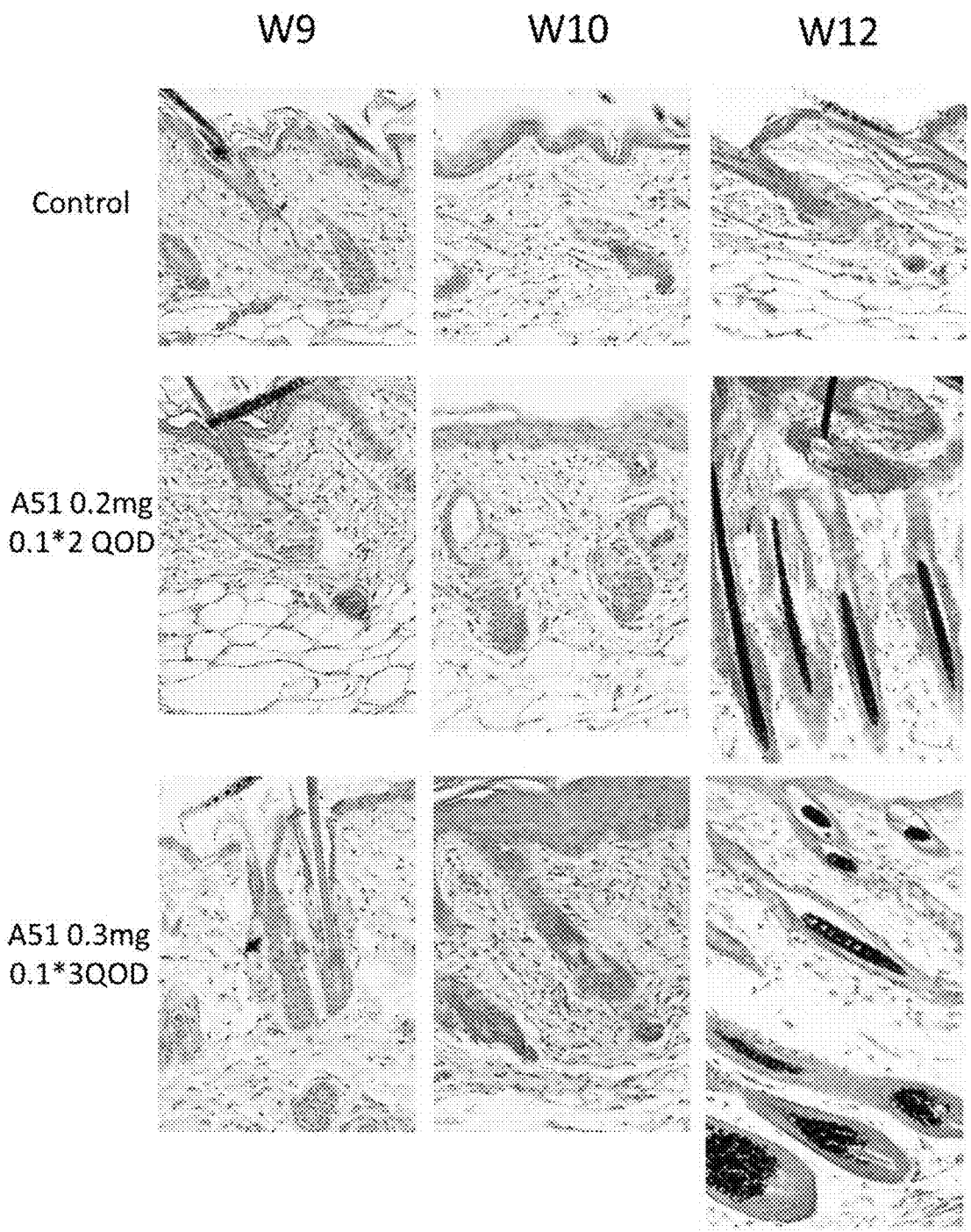
Figure 4F:
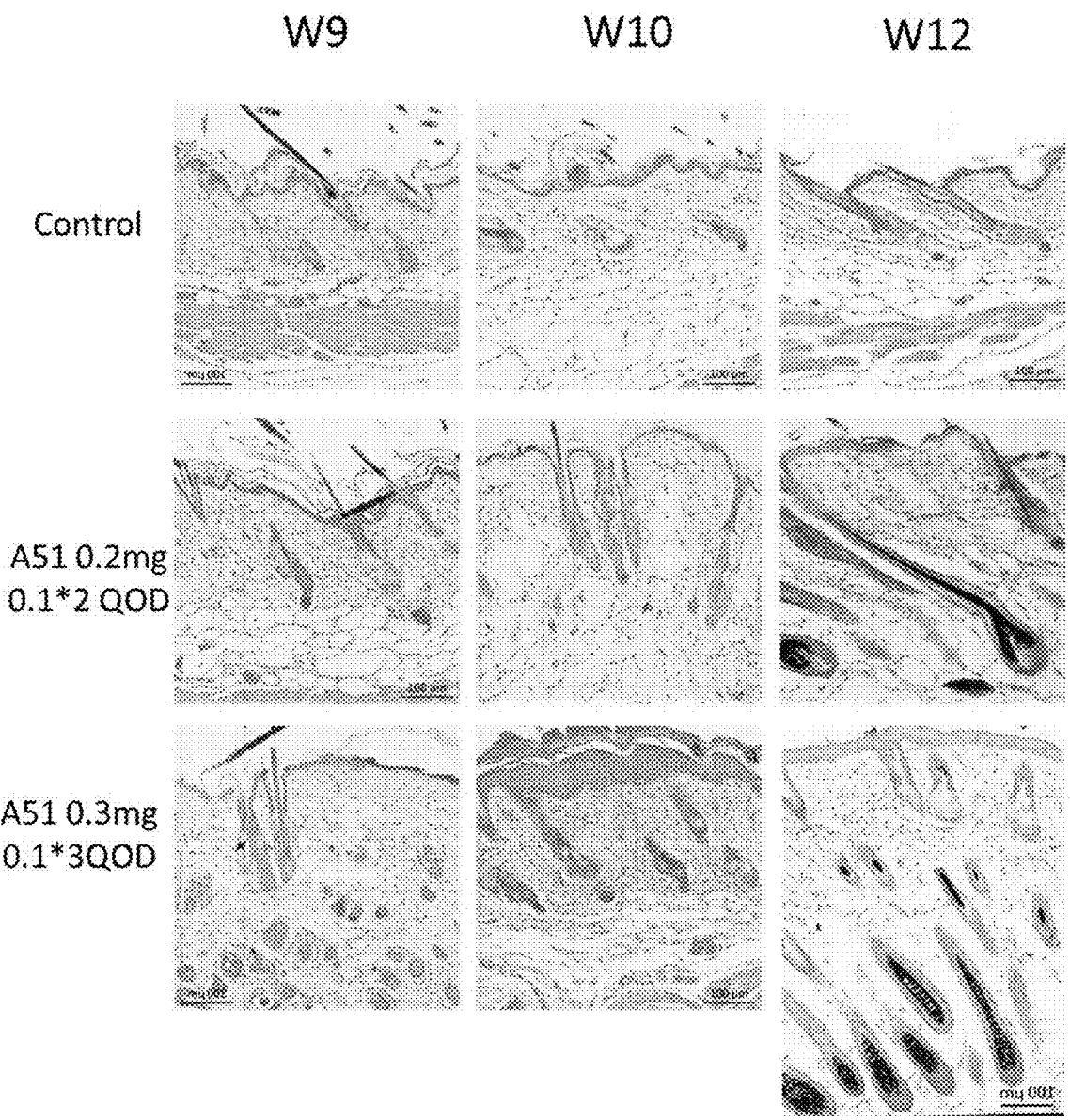

In addition, topical application of CK1α inhibitors on wild-type mice were carried out to inhibit CK1α expression in mice back skin. As shown in FIG. 4A, topical CK1α inhibitor, e.g., A51, at a concentration of 0.1 mg/cm$^2$ were given 2 or 3 times on the shaved back skin of mice at 8 weeks old. FIG. 4B shows starting of hair growth on the backs of mice topically treated with CK1α inhibitor A51 as early as in week 9 with most of the mice back covered with hair in week 12. FIG. 4C shows the H&E staining of back skins, and it was found that in the control group, hair follicles remained in a telogen phase during weeks 9, 10 and 12. However, an induced anagen phase was observed at week 9 in mice topically treated with 0.2 mg CKI at week 8, and mice topically treated with 0.3 mg CKI were induced with more advanced stage of anagen at week 9, with heavy pigmented hair shaft observed at week 12. That is to say, topical application of CK1α inhibitor is also able to induce and initiate an anagen phase of hair follicles from a telogen phase. FIG. 4D shows the result of immunohistochemical staining of β-catenin. Topical application of the CK1α inhibitor increased the expression of β-catenin in the hair germ, outer root sheath and epidermis, as compared to control mice. FIG. 4E shows the result of Fontana-Masson staining, which shows hair follicle pigmentation in CK1α treated skin in addition to hair growth. Therefore, topical application of the CK1α inhibitor induces hair follicle growth and pigmented hair formation.

Figure 5A:
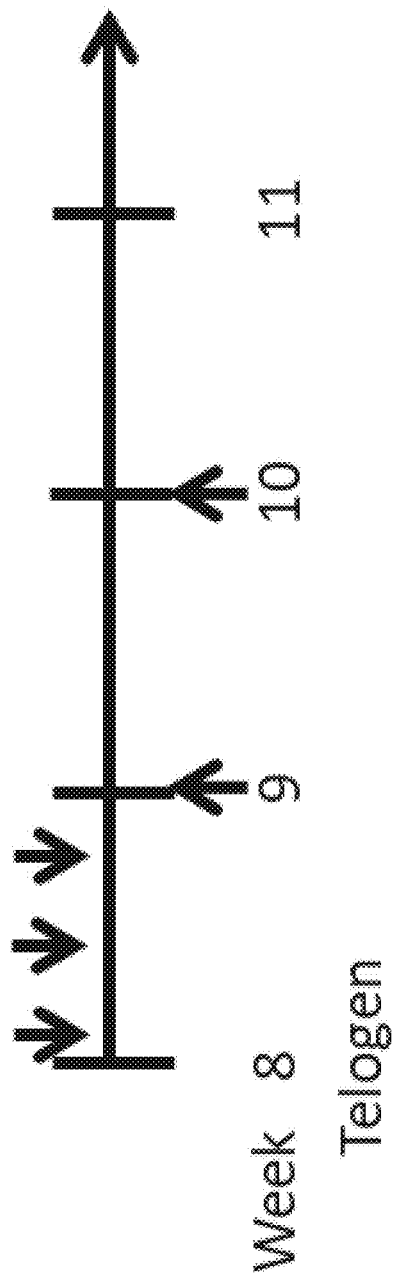
FIGS. 5A to 5E show CK1α inhibitors D4476 and IC261 in inducing hair growth and pigmentation in C57/BL6 wild-type mice at 8 weeks old.
Figure 5B:
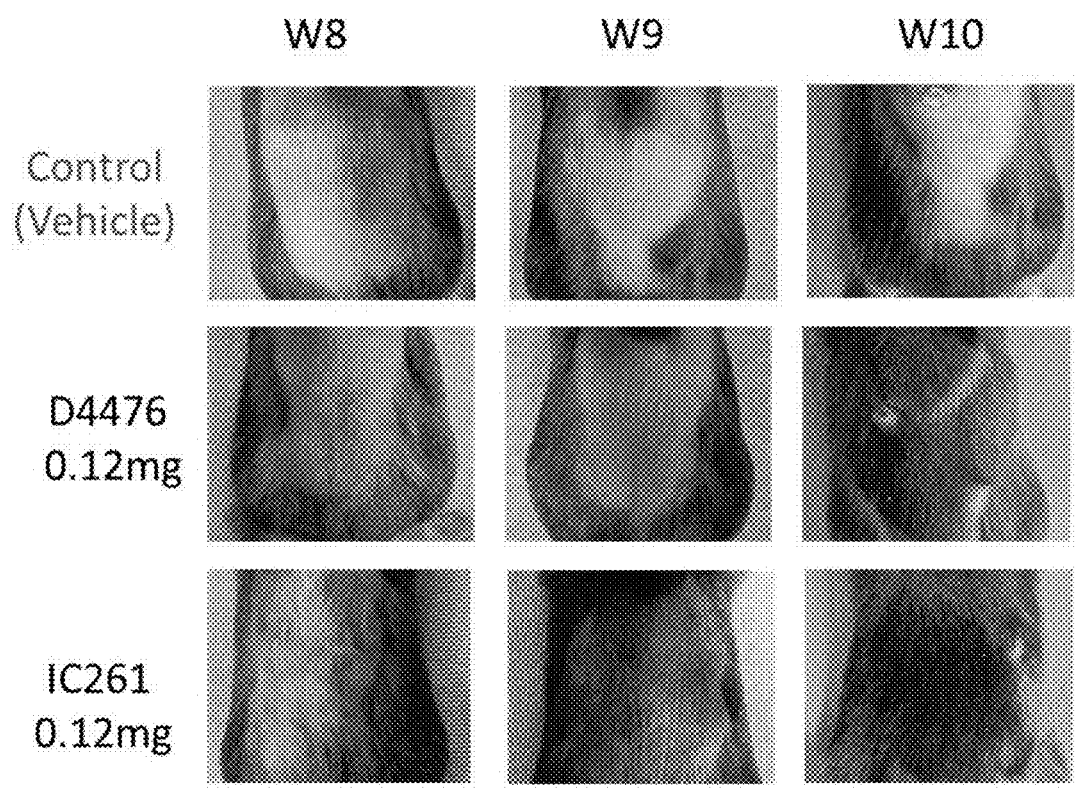
Figure 5C:
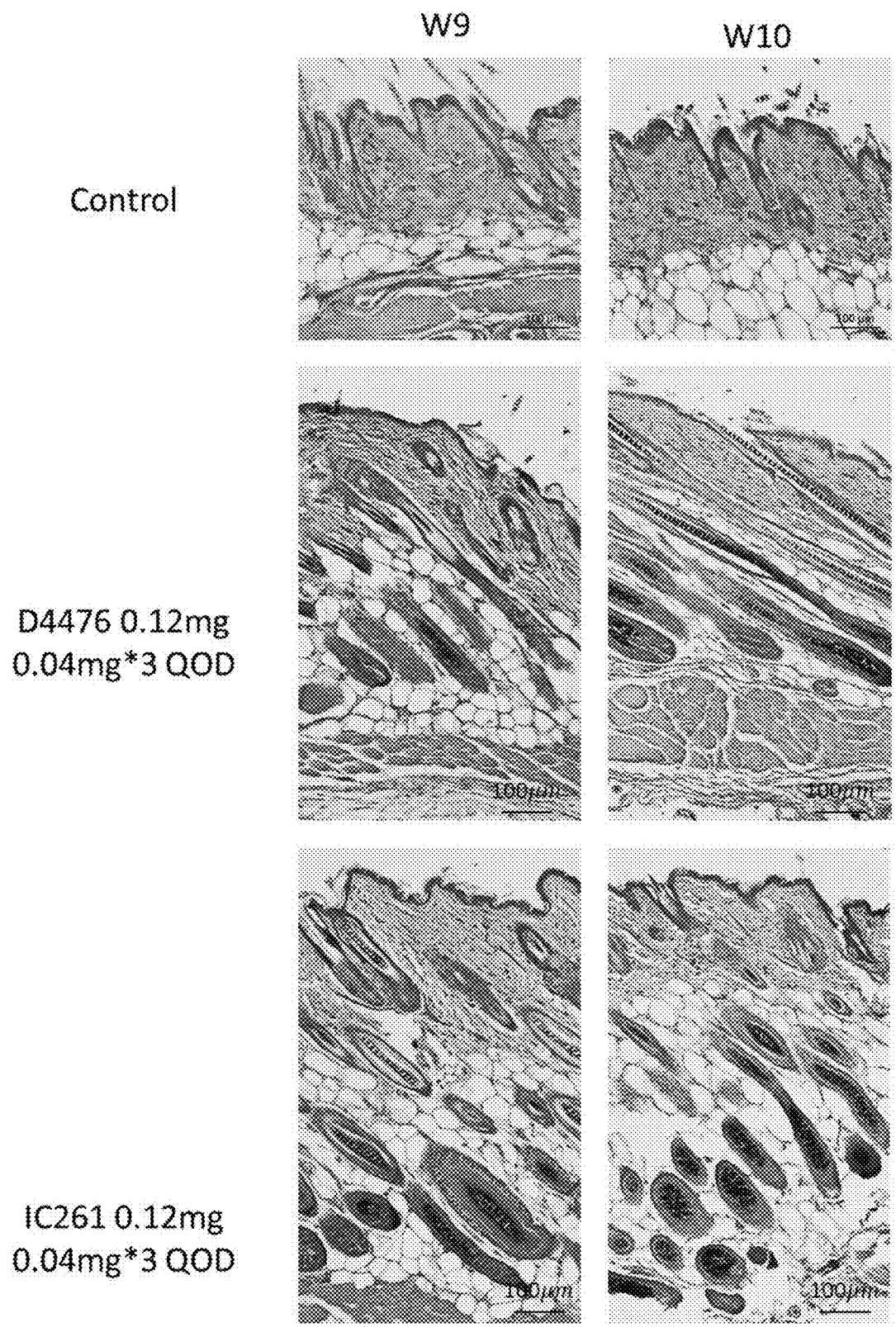
Figure 5D:
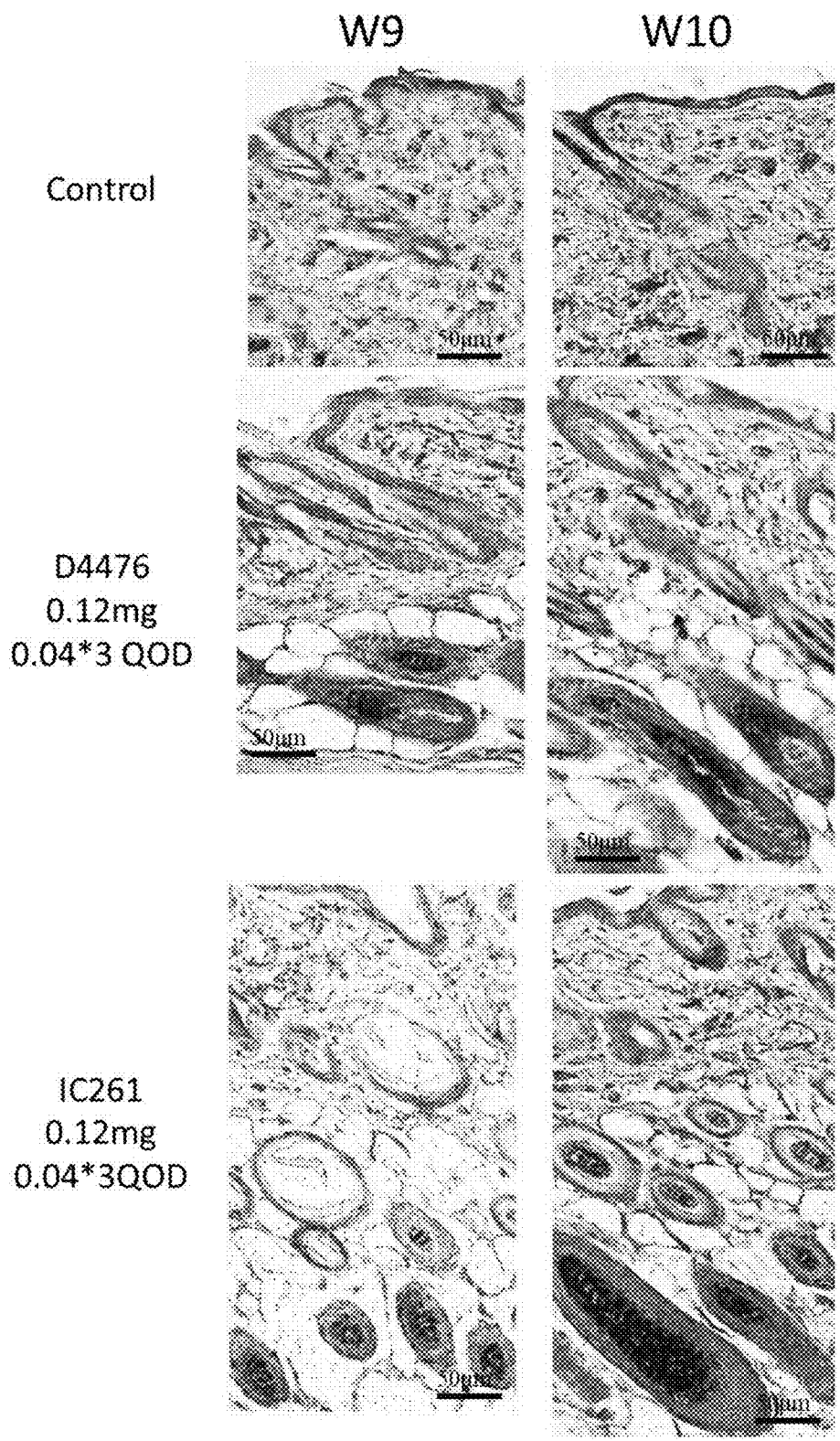
Figure 5E:
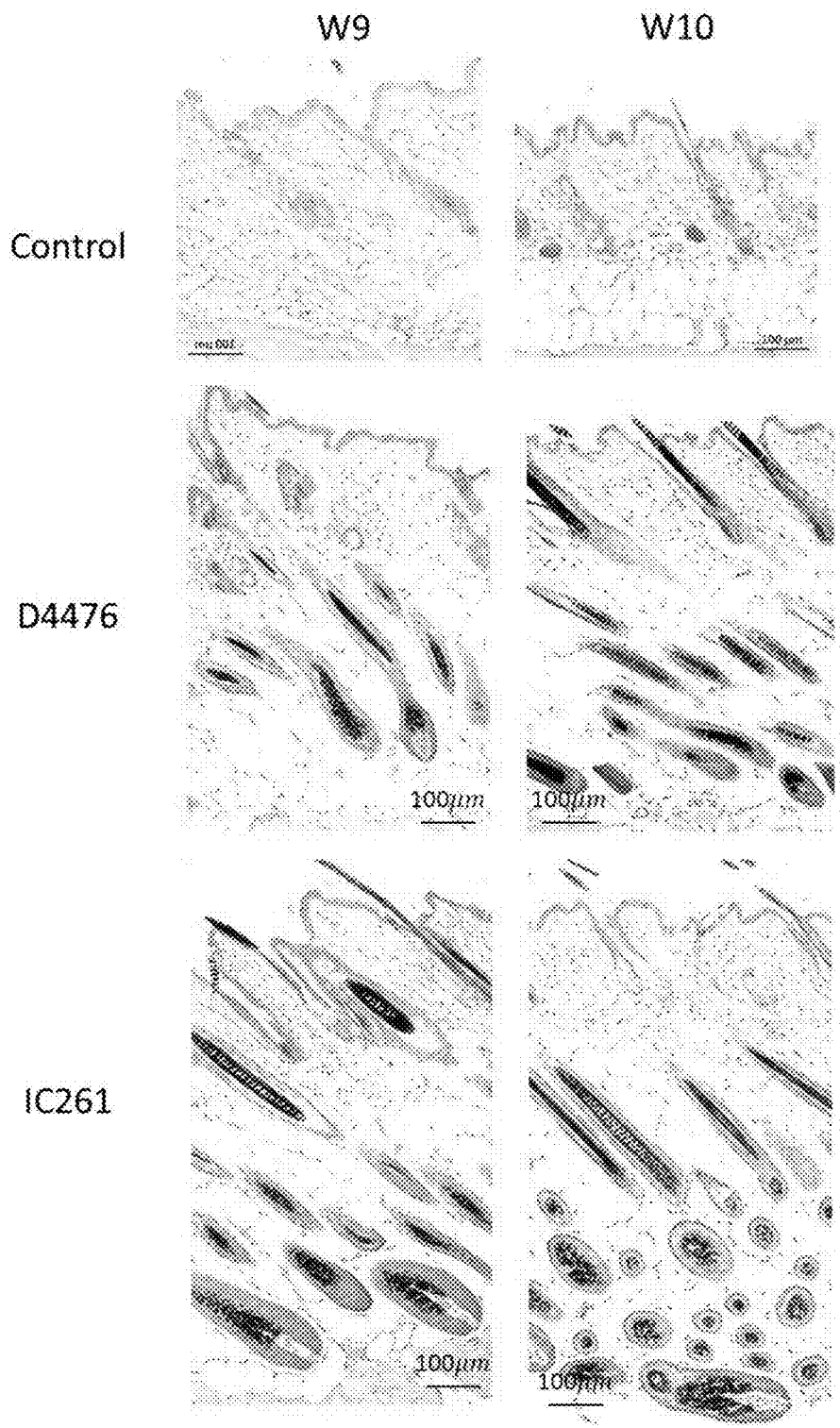

Other CK1α inhibitors including D4476 and IC261 were also tested. As shown in FIG. 5A, the CK1α inhibitors, D4476 and IC261, were topically applied to the shaved back skin of mice at 8 weeks old every other day, three times per week, with a total dose of 0.12 mg per 1 cm² of the back skin. FIG. 5B shows that topical application of D4476 or IC261 significantly induced hair growth on the back skin of the treated mice (N=3), which is a result of a hair cycle moving into anagen from telogen. FIG. 5C shows the H&E staining of back skins and it was found that topical application of a CK1α inhibitor induces an anagen phase of the hair cycle and observed formation of hair follicles showing characteristic of an anagen phase. FIG. 5D shows the result of immunohistochemical staining of β-catenin. Topical application of CK1α inhibitors, D4476 and IC261, also increased the expression of β-catenin in the matrix of hair follicle. FIG. 5E shows the result of Fontana-Masson staining with topical application of additional CK1α inhibitors such as D4476 and IC261 that induce hair follicle growth and pigmented hair formation.

Example 2: Inhibition of CK1α Prolongs an Anagen Phase in a Hair Cycle

Figure 6A:
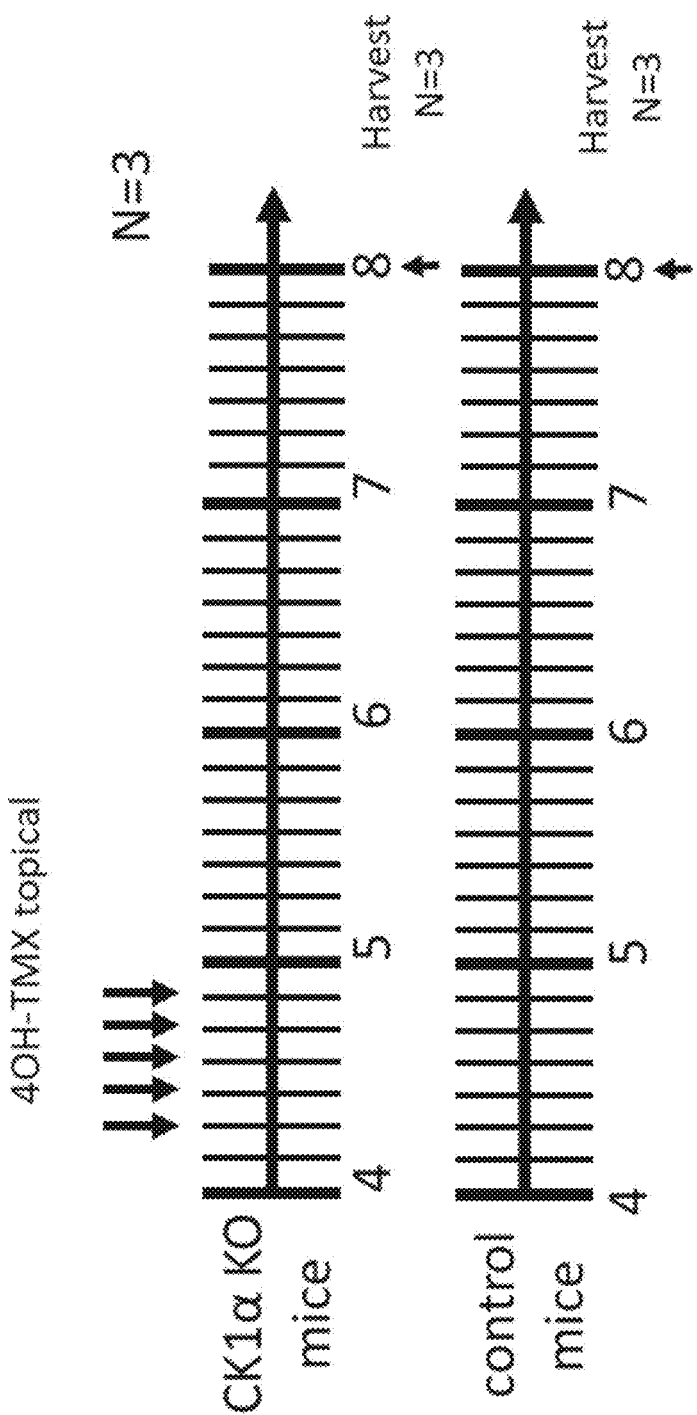
FIGS. 6A to 6C show that inhibition of CK1α prolongs an anagen phase in a hair cycle.
Figure 6B:
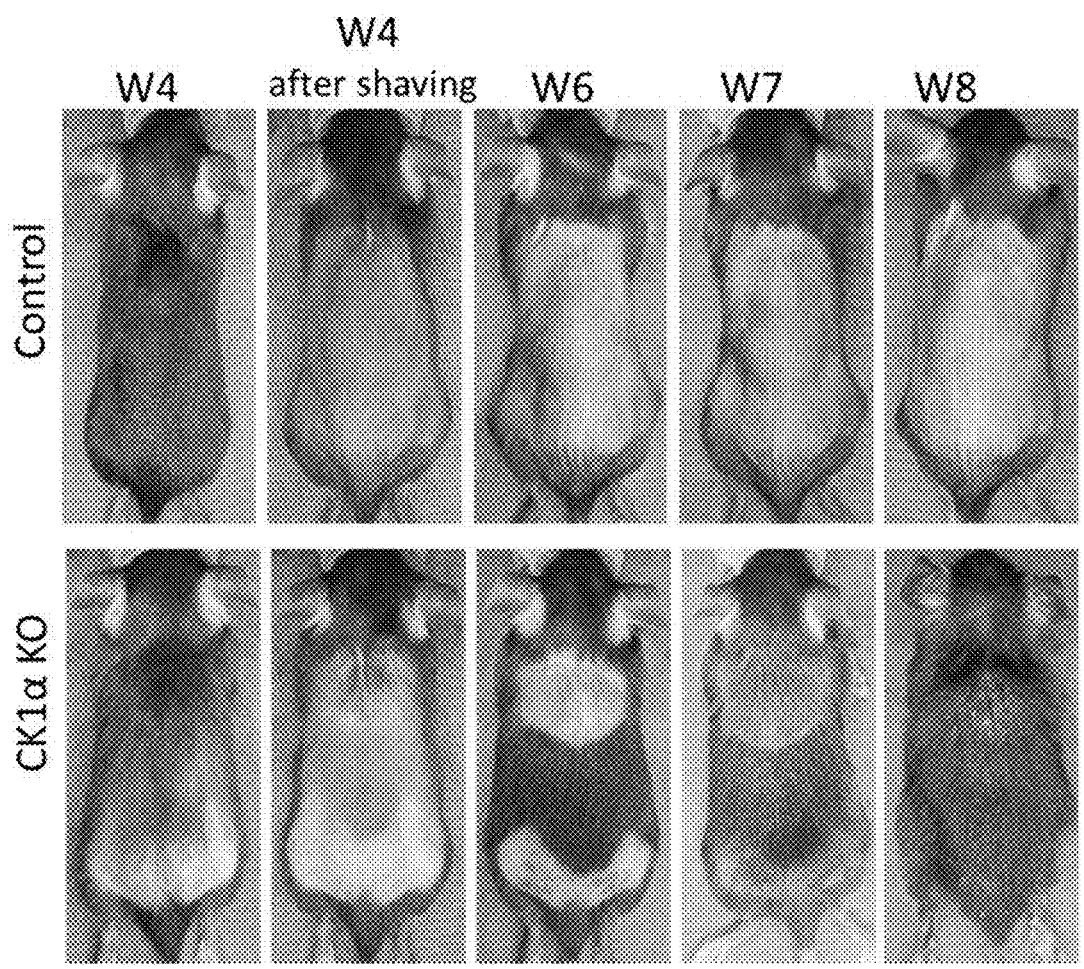
Figure 6C:
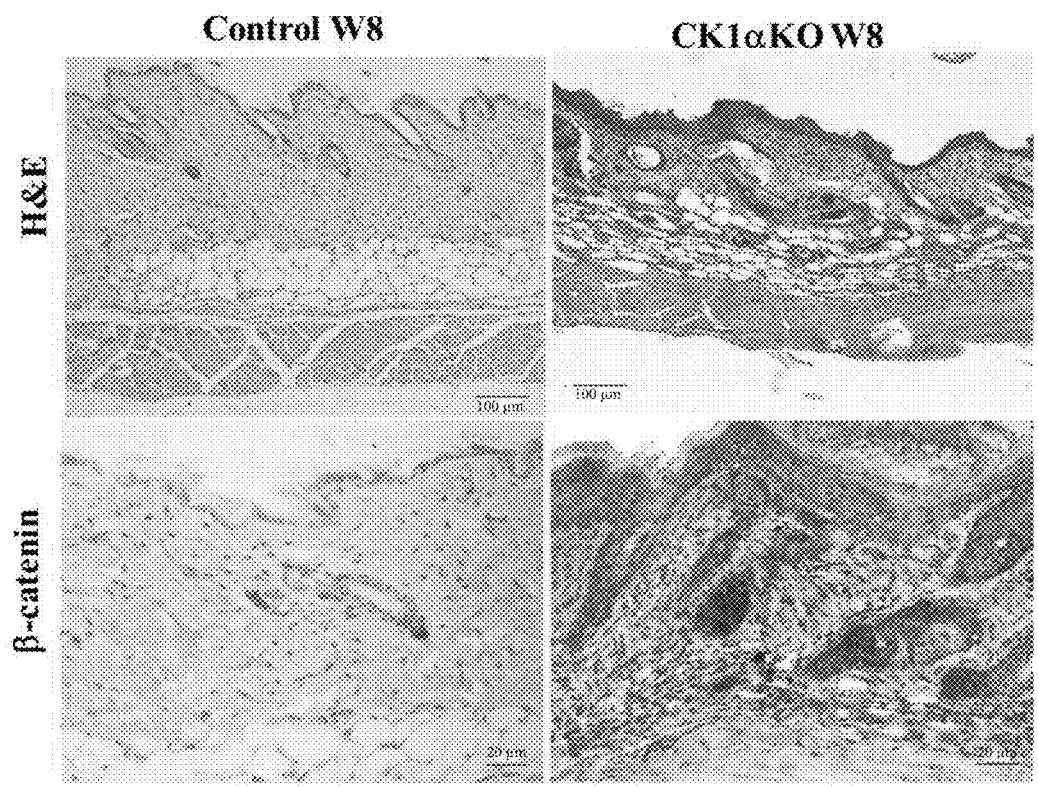

CK1α ablation carried out during an anagen phase of keratinocytes was found to increase the duration of an anagen phase in a hair cycle. 4-OH-TMX was used for topical induction of CK1α ablation in keratinocytes of the back skins of 4-weeks-old K14-Cre-ERT2-CK1α$^{fl/fl}$ mice, as shown in FIG. 6A. Phenotypes were recorded from week 4 to week 8. As shown in FIG. 6B, it was found that in control mice (N=6), an anagen phase lasted from week 4 to week 5, followed by week 6 in a catagen phase, and stayed in a telogen phase from week 7 to week 8. In CK1α ablation mice (N=6), hairs appeared and started to cover the shaved back skins in weeks 6 to 8, indicating the anagen phase was prolonged. FIG. 6C shows the H&E staining and β-catenin staining of mice at week 8. It was found that control mice were in a telogen phase at week 8, but CK1α-ablated mice were still in an anagen phase at week 8 with enhanced β-catenin staining in the matrix of hair follicles.

Example 3: Inhibition of CK1α Increases Hair Pigmentation

Inhibition of CK1α in keratinocytes was also found to increase pigmentation of hair. CK1α inhibitors including A51, D4476 and IC261 were topically applied to shaved back skin of mice at week 8, when the hair cycle was during the telogen phase. Then, Masson-Fontana staining was carried for assessing pigmentation of hair. Heavily pigmented hair follicles and shafts were found in hairs of the mice topically treated with A51, as shown in FIG. 4E, and also in hairs of the mice topically treated with D4476 and IC261, as shown in FIG. 5E.

Figure 7A:
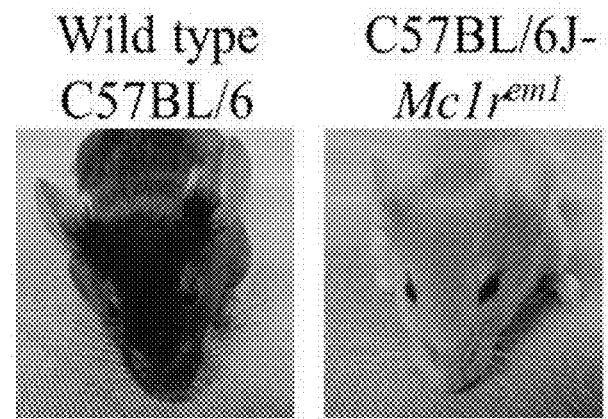
Figure 7A:
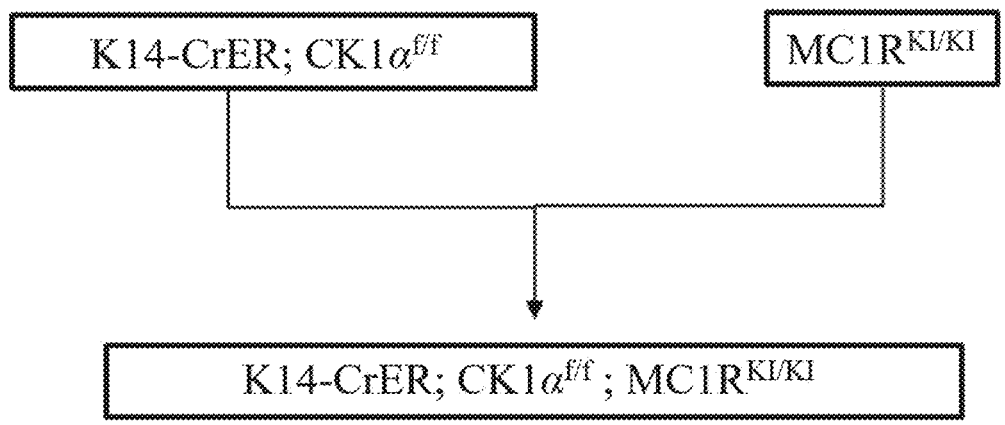
Figure 7B:
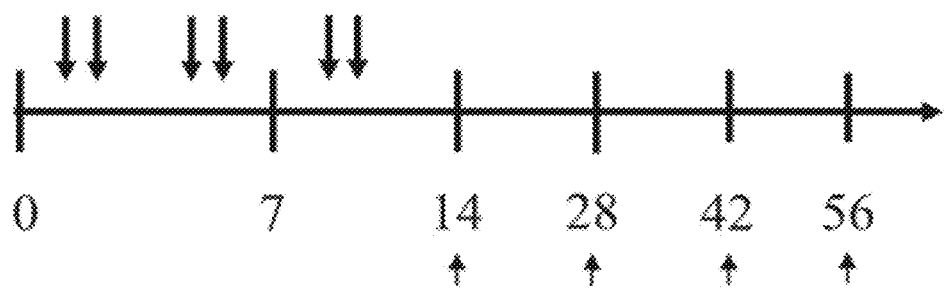
Figure 7C:
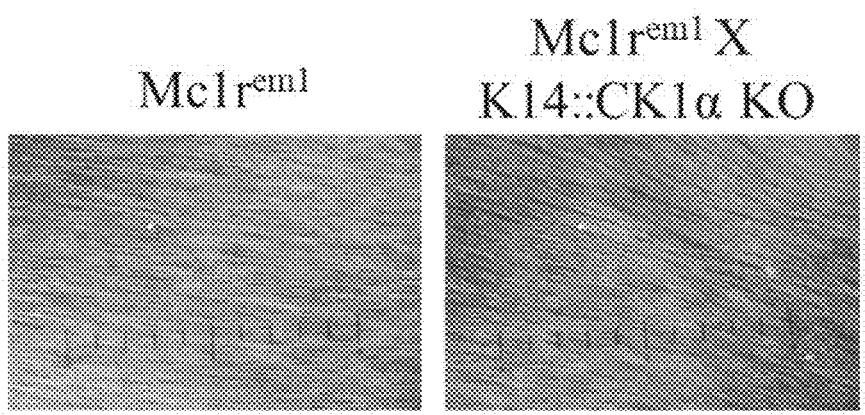
Figure 7E:
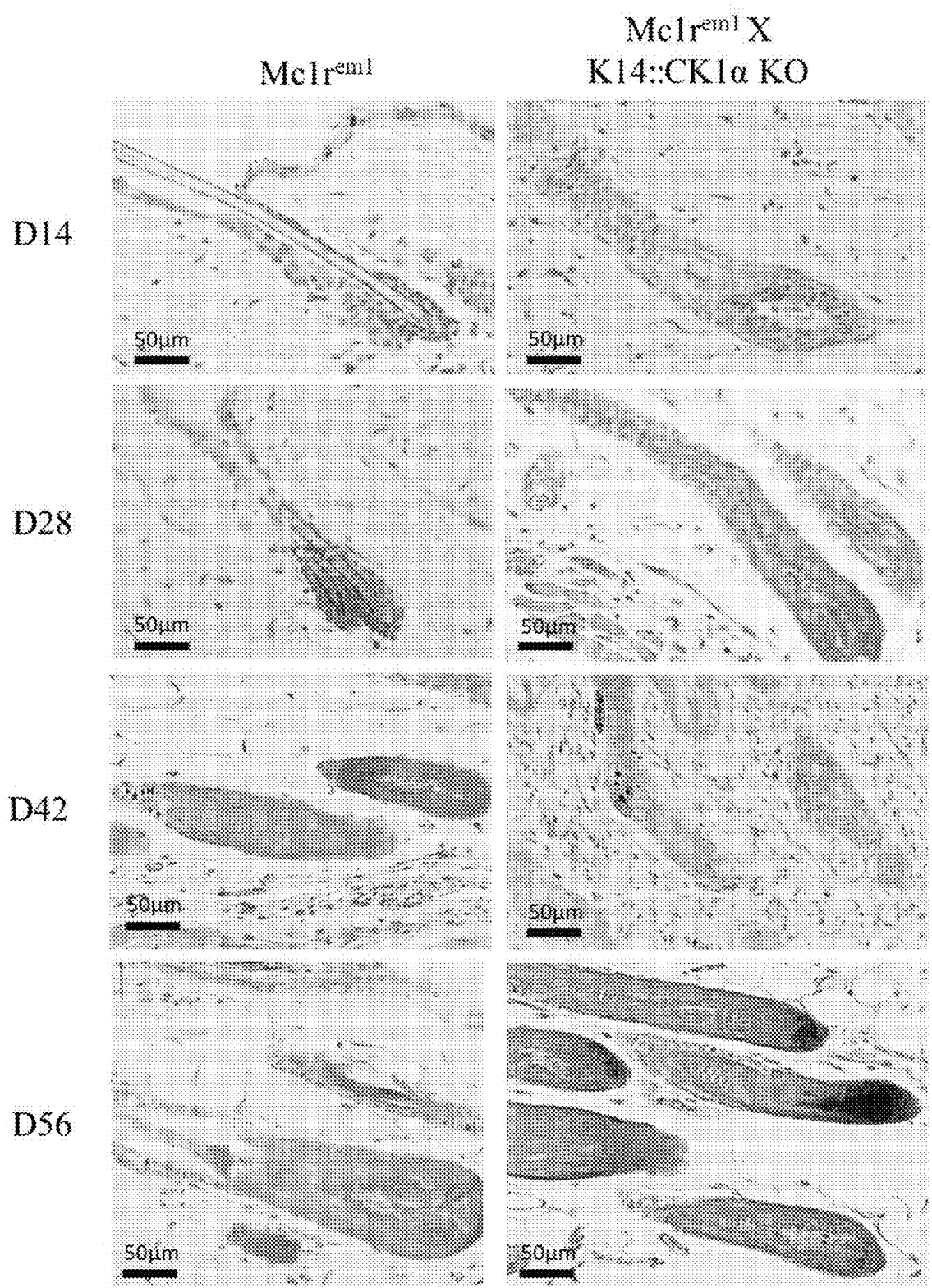
Figure 7F:
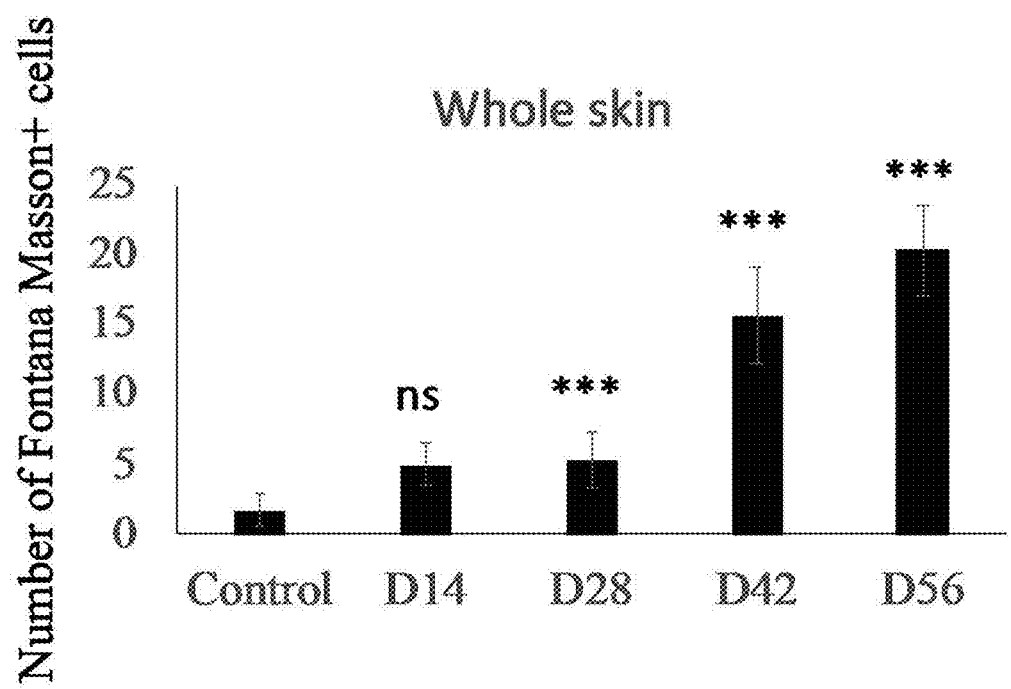
Figure 7G:
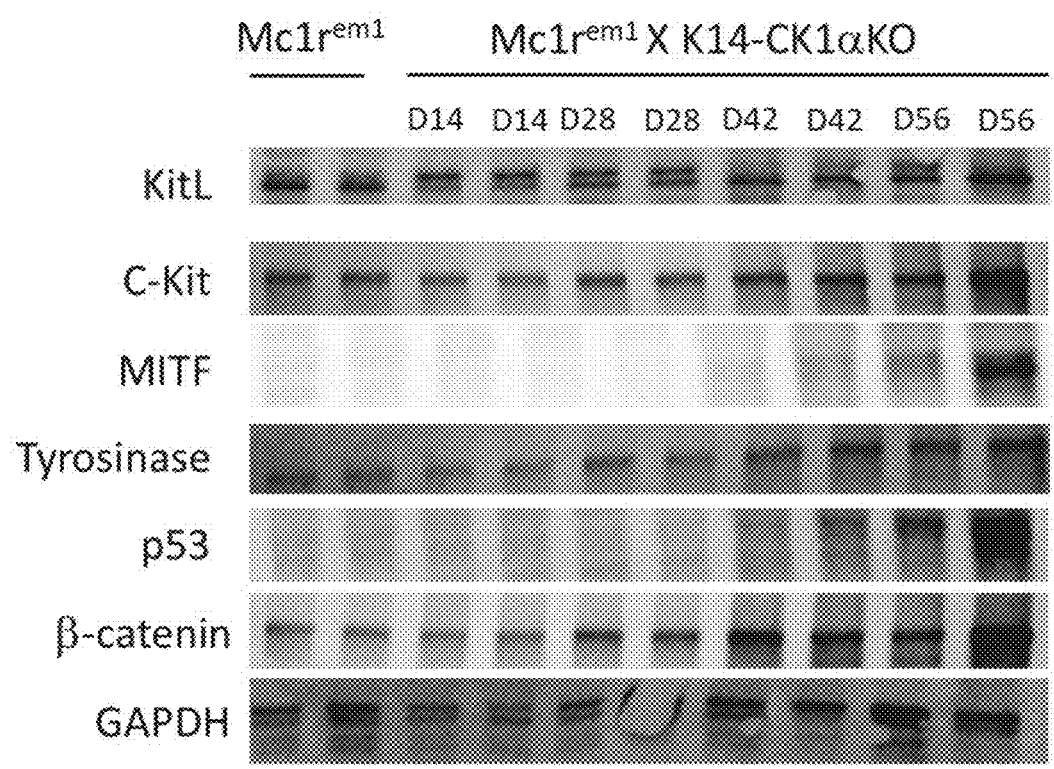
Figure 7H:
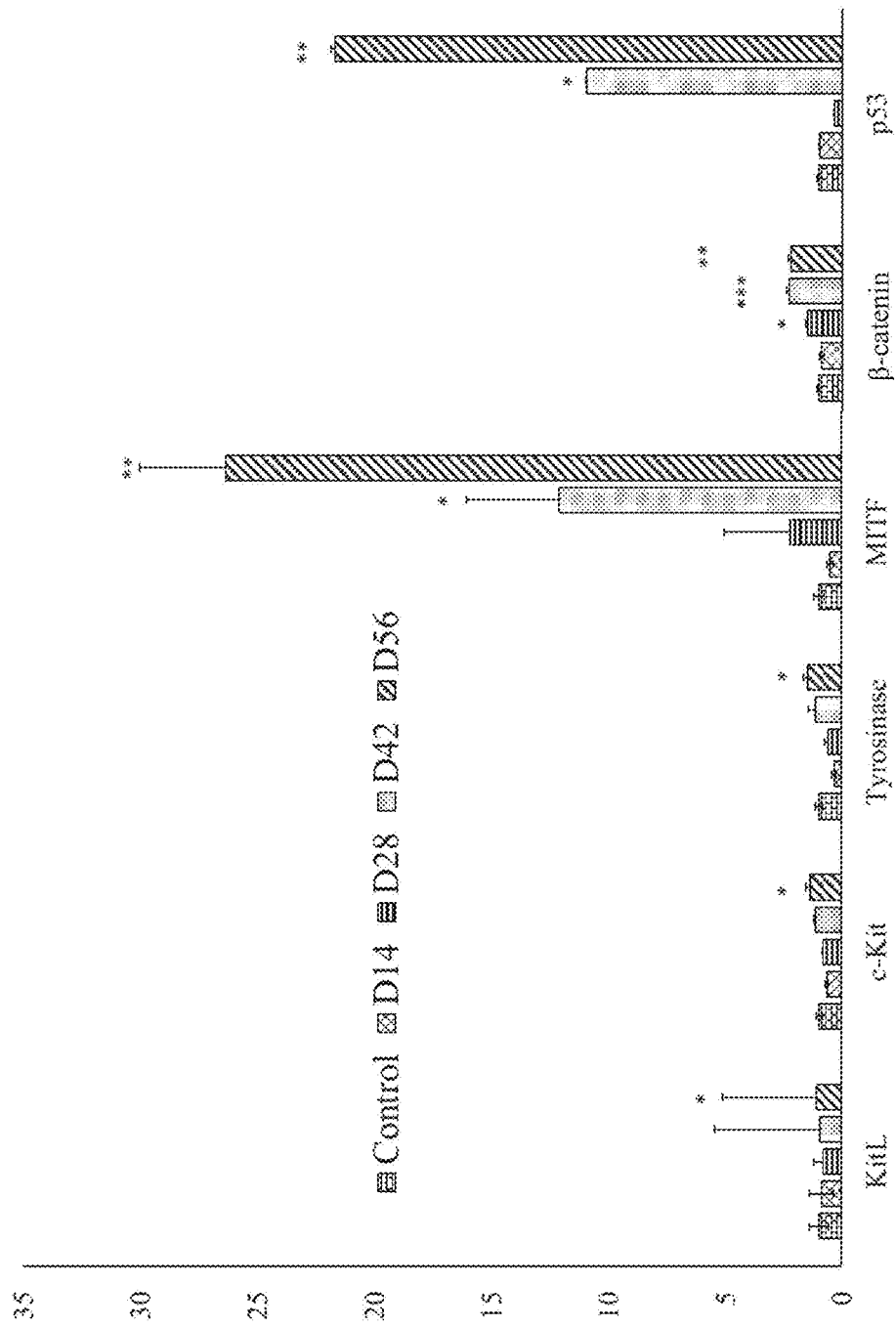

In addition to wild-type mice (black C57BL/6), MC1R mutated mice were also used as an animal model to show increase of hair pigmentation by inhibition of CK1α. The MC1R mutated mice having a deletion of a single nucleotide at position 549 of MC1R that leads to 12 amino acids out-of-frame mutation have been reported by Mountjoy, Robbins et al. 1992. The C57BL/6J-Mc1r$^{em1}$ mice carrying a deletion of a single nucleotide at position 549 in the MC1R gene were generated previously by a CRISPR/Cas9 system. The deletion causes a frame-shift mutation and leads to loss of function of the MC1R protein, resulting in a yellow coat color in mice, due to exclusive synthesis of pheomelanin and failure to synthesize eumelanin by the melanocytes, as shown in the photograph of FIG. 7A. The MC1R mutated mouse was then crossed with K14-CreER;CK1α$^{fl/fl}$ mouse to generate K14-CreER;CK1α$^{fl/fl}$;MC1R$^{KI/KI}$ mouse, which can be induced to ablate CK1α in keratinocytes. As shown in FIG. 7B, 7-weeks-old mice were subjected to induction with intraperitoneal injection of tamoxifen at 100 mg/kg for a total of 6 times at days 1, 2, 5, 6, 8 and 9. Skin samples were harvested at days 14, 28, 42 and 56 for analysis. As shown in FIG. 7C, increased pigmentation of hairs was noted on MC1R mutated mice with CK1α a ablation in keratinocytes on day 28, compared to MC1R mutated mice. The dissection microscopy results shown in FIG. 7D present a closer and clearer view on increased hair shaft pigmentation of MC1R mutated mice with CK1α a ablation in keratinocytes, on days 14 and 28, in comparison to MC1R mutated mice. FIG. 7E shows the Fontana-Masson staining of the skin samples. It was shown that eumelanin intensity in the matrix and inner root sheath was increased, demonstrated by a time course analysis on MC1R mutated mice with CK1α ablation in keratinocytes, which is not observed in MC1R mutated mice. FIG. 7F shows the quantitated number of cells stained by Fontana-Masson staining in FIG. 7E. FIGS. 7G and 7H show the Western blotting result and the corresponding quantitated expression levels, revealing stabilization of β-catenin and p53, and upregulation of KitL, c-Kit, MITF and tyrosinase. The KitL/C-Kit pathway was upregulated for the pigmentation of hair.

The present disclosure has been described with embodiments thereof, and it is understood that various modifications, without departing from the scope of the present disclosure, are in accordance with the embodiments of the present disclosure. Hence, the embodiments described are intended to cover the modifications within the scope of the present disclosure, rather than to limit the present disclosure. The scope of the claims therefore should be accorded the broadest interpretation so as to encompass all such modifications.

What is claimed is:

1. A method for enhancing hair growth on an area of skin in a subject having delayed or slow growth of hair or premature falling of hair, comprising topically administering to the subject a casein kinase 1 inhibitor selected from the group consisting of D4476, IC261, CKI7, a compound represented by following general formula I, a compound of following formula II, a compound of following formula III, a compound of following formula IV, a compound of following formula V, and a compound of following formula VI:

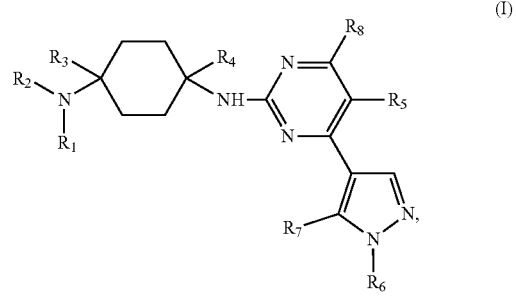

wherein:

R₁ and R₂ are each independently selected from the group consisting of H, straight or branched C1-C8 alkyl, straight or branched C1-C5 alkoxy, straight or branched C1-C5 acyl, C5-C15 aryl, and C3-C7 heteroaryl each optionally substituted by at least one of halide, hydroxyl, ester, ether, C5-C15 aryl, C3-C7 heteroaryl, and amide; or R₁ and R₂ together with the nitrogen atom they are connected to form a 4 to 7 membered saturated, unsaturated or aromatic ring optionally including at least one of N, O, NH, C=N, C=O and SO₂ and optionally substituted with at least one of straight or branched C1-C5 alkyl, C5-C15 aryl, C3-C7 heteroaryl, hydroxyl, halide and cyano;

R₃ and R₄ are each independently selected from the group consisting of H, straight or branched C1-C8 alkyl optionally substituted by at least one of halide, hydroxyl, alkoxy, C5-C15 aryl, C3-C7 heteroaryl, ester and amide; or R₁ or R₂ together with R₃ and the carbon and nitrogen atom they are each connected to form a 4 to 7 membered saturated, unsaturated or aromatic ring optionally including at least one of N, NH, O, C=N, C=O, and SO₂, and optionally substituted with at least one of straight or branched C1-C5 alkyl, C5-C15 aryl, C3-C7 heteroaryl, hydroxyl, carbonyl, and halide;

R₅ and R₈ are each independently selected from the group consisting of H, halide, straight or branched C1-C8 alkyl, straight or branched C2-C8 alkenyl, and straight or branched C2-C8 alkynyl optionally substituted by at least one halide;

R₆ is selected from straight or branched C1-C8 alkyl, straight or branched C2-C8 alkenyl, straight or branched C2-C8 alkynyl, C5-C10 cycloalkyl, and saturated or unsaturated 4 to 6 membered heterocycle optionally substituted by at least one of straight or branched C1-C8 alkyl, C3-C7 cycloalkyl, 4 to 6 membered heterocycle, C5-C15 aryl, C3-C7 heteroaryl, halide, hydroxyl, and C1-C5 alkyl halide;

R₇ is selected from the group consisting of straight or branched C1-C8 alkyl, straight or branched C2-C8 alkenyl, and straight or branched C2-C8 alkynyl optionally substituted by at least one of C3-C7 cycloalkyl, 4 to 6 membered heterocycle, C5-C15 aryl, C3-C7 heteroaryl, halide, hydroxyl, and C1-C5 alkyl halide;

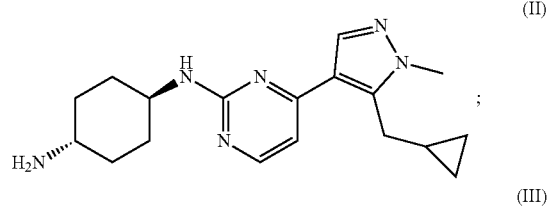

(II)

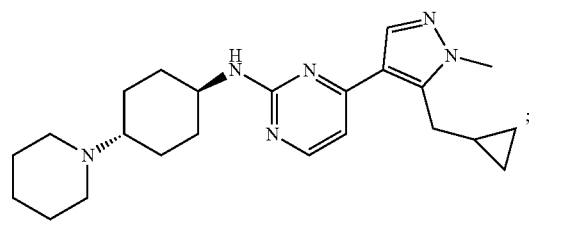

(III)

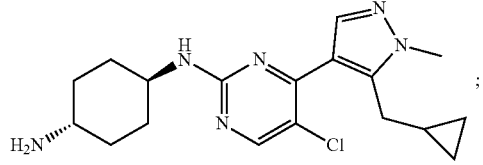

(IV)

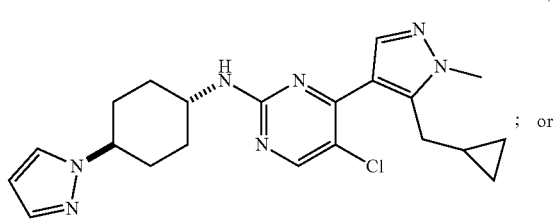

(V)

; or

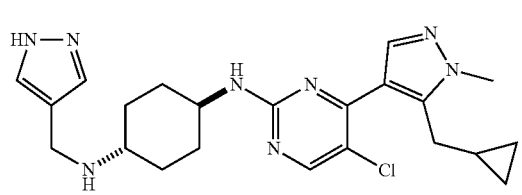

(VI)

2. The method of claim 1, wherein the subject suffers from hair loss.

3. The method of claim 2, wherein the hair loss is a hair loss caused by nutritional deficiency, a drug-induced hair loss, a radiation-induced hair loss, a stress-induced hair loss, a genetic hair loss, an aging hair loss or a disease-induced hair loss.

4. The method of claim 3, wherein the drug-induced hair loss is induced by a chemotherapy drug, lithium, arsenic, bismuth, boric acid, thallium, colchicine, retinoid, heparin, warfarin, β-blocker, an angiotensin-converting enzyme (ACE) inhibitor, a hormone, valproic acid, carbamazepine, phenytoin, cimetidine, an antithyroid drug, a cholesterol-lowering drug, interferon, an anti-infective agent, amphetamine, an antidepressant, an anti-fungal agent, an anti-seizure agent, a birth control agent, a vitamin A-based medication, a medication for Parkinson's disease, a medication for stomach or a nonsteroidal anti-inflammatory drug.

5. The method of claim 3, wherein the disease-induced hair loss is caused by an autoimmune disease, a thyroid disorder, a metabolic syndrome, an infection or a cancer.

6. The method of claim 5, wherein the autoimmune disease is alopecia areata, lupus erythematosus, Sicca syndrome, scleroderma, Crohn's disease, inflammatory bowel disease or psoriasis.

7. The method of claim 1, wherein the subject suffers from alopecia.

8. The method of claim 7, wherein the alopecia is selected from the group consisting of androgenetic alopecia, alopecia areata, anagen effluvium, self-induced hair loss, telogen effluvium, and scarring alopecia.

9. The method of claim 1, wherein the inhibition comprises inhibiting gene expression of the casein kinase 1α in the area of skin.

10. A method for increasing hair pigmentation in an area of skin in a subject in need thereof, comprising topically administering to the subject a casein kinase 1 inhibitor selected from the group consisting of D4476, IC261, CKI7, a compound represented by following general formula I, a compound of following formula II, a compound of following formula III, a compound of following formula IV, a compound of following formula V, and a compound of following formula VI:

(I)

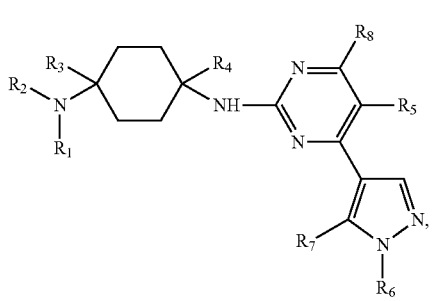

wherein:
R₁ and R₂ are each independently selected from the group consisting of H, straight or branched C1-C8 alkyl, straight or branched C1-C5 alkoxy, straight or branched C1-C5 acyl, C5-C15 aryl, and C3-C7 heteroaryl each optionally substituted by at least one of halide, hydroxyl, ester, ether, C5-C15 aryl, C3-C7 heteroaryl, and amide; or R₁ and R₂ together with the nitrogen atom they are connected to form a 4 to 7 membered saturated, unsaturated or aromatic ring optionally including at least one of N, O, NH, C=N, C=O and SO₂ and optionally substituted with at least one of straight or branched C1-C5 alkyl, C5-C15 aryl, C3-C7 heteroaryl, hydroxyl, halide and cyano;
R₃ and R₄ are each independently selected from the group consisting of H, straight or branched C1-C8 alkyl optionally substituted by at least one of halide, hydroxyl, alkoxy, C5-C15 aryl, C3-C7 heteroaryl, ester and amide; or
R₁ or R₂ together with R₃ and the carbon and nitrogen atom they are each connected to form a 4 to 7 membered saturated, unsaturated or aromatic ring optionally including at least one of N, NH, O, C=N, C=O, and SO₂, and optionally substituted with at least one of straight or branched C1-C5 alkyl, C5-C15 aryl, C3-C7 heteroaryl, hydroxyl, carbonyl, and halide;
R₅ and R₈ are each independently selected from the group consisting of H, halide, straight or branched C1-C8 alkyl, straight or branched C2-C8 alkenyl, and straight or branched C2-C8 alkynyl optionally substituted by at least one halide;
R₆ is selected from straight or branched C1-C8 alkyl, straight or branched C2-C8 alkenyl, straight or branched C2-C8 alkynyl, C5-C10 cycloalkyl, and saturated or unsaturated 4 to 6 membered heterocycle optionally substituted by at least one of straight or branched C1-C8 alkyl, C3-C7 cycloalkyl, 4 to 6 membered heterocycle, C5-C15 aryl, C3-C7 heteroaryl, halide, hydroxyl, and C1-C5 alkyl halide;
R₇ is selected from the group consisting of straight or branched C1-C8 alkyl, straight or branched C2-C8 alkenyl, and straight or branched C2-C8 alkynyl optionally substituted by at least one of C3-C7 cycloalkyl, 4 to 6 membered heterocycle, C5-C15 aryl, C3-C7 heteroaryl, halide, hydroxyl, and C1-C5 alkyl halide;

(II)

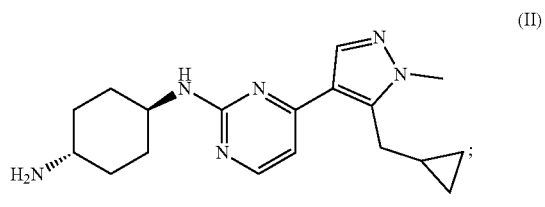

(III)

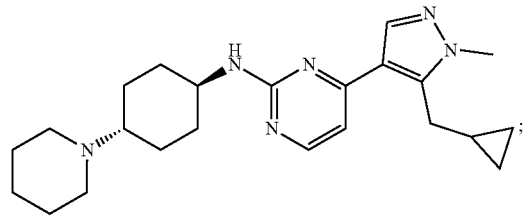

(IV)

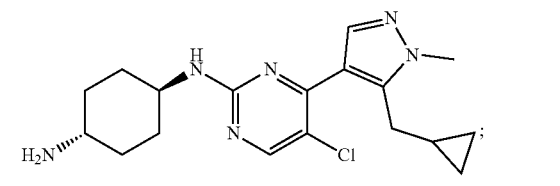

(V)

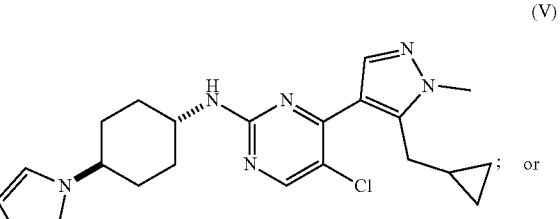

; or (VI)

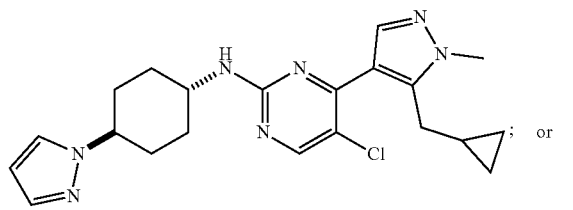

11. The method of claim 10, wherein the area of skin comprises graying hair.

* * * * *